US010822393B2

(12) United States Patent
Winge et al.

(10) Patent No.: US 10,822,393 B2
(45) Date of Patent: Nov. 3, 2020

(54) PROCESS FOR MANUFACTURING FACTOR VIII HAVING AN IMPROVED RATIO OF FVIII:C/FVIII/AG

(71) Applicant: OCTAPHARMA AG, Lachen (CH)

(72) Inventors: Stefan Winge, Stockholm (SE);
Marina Dadaian, Stockholm (SE);
Erica Johansson, Stockholm (SE);
Birte Fuchs, Berlin (DE)

(73) Assignee: OCTAPHARMA AG, Lache (CH)

( * ) Notice: Subject to any disclaimer, the term of this patent is extended or adjusted under 35 U.S.C. 154(b) by 0 days.

(21) Appl. No.: 15/112,936

(22) PCT Filed: Jan. 20, 2015

(86) PCT No.: PCT/EP2015/051028
§ 371 (c)(1),
(2) Date: Jul. 20, 2016

(87) PCT Pub. No.: WO2015/107222
PCT Pub. Date: Jul. 23, 2015

(65) Prior Publication Data
US 2016/0340410 A1 Nov. 24, 2016

(30) Foreign Application Priority Data
Jan. 20, 2014 (EP) ..................................... 14151769

(51) Int. Cl.
*C07K 14/755* (2006.01)
*C07K 1/22* (2006.01)
*C07K 1/18* (2006.01)
*A61K 38/37* (2006.01)
*A61K 38/00* (2006.01)

(52) U.S. Cl.
CPC .............. *C07K 14/755* (2013.01); *C07K 1/22* (2013.01); *A61K 38/00* (2013.01)

(58) Field of Classification Search
None
See application file for complete search history.

(56) References Cited

U.S. PATENT DOCUMENTS

| 4,675,385 A | 6/1987 | Herring |
| 8,187,799 B2 | 5/2012 | Tsvetkova et al. |

FOREIGN PATENT DOCUMENTS

| CA | 1341169 C | 1/2001 |
| CA | 2673459 A1 | 7/2008 |
| EP | 0412466 A2 | 2/1991 |
| EP | 1136553 A1 | 9/2001 |
| EP | 1739179 A1 | 1/2007 |
| EP | 2537862 A1 | 12/2012 |
| FR | 2650393 A1 | 2/1991 |
| RU | 2423380 C2 | 7/2011 |
| WO | WO-1997/33178 A1 | 9/1997 |
| WO | 2006053299 A2 | 5/2006 |
| WO | WO-2008/134310 A1 | 11/2008 |
| WO | WO-2009/156430 A1 | 12/2009 |
| WO | WO-2010/026186 A1 | 3/2010 |
| WO | WO-2010/115866 A1 | 10/2010 |
| WO | WO-2015/107222 | 2/2015 |

OTHER PUBLICATIONS

Boedeker, Production processes of licensed recombinant factor VIII preparations, Seminars in thrombosis and hemostasis, 2001; 27(4):385-94.
Bradford, A rapid and sensitive method for the quantitation of microgram quantities of protein utilizing the principle of protein-dye binding. Anal Biochem. 1976; 72(1-2):248-54.
Casademunt et al., The first recombinant human coagulation factor VIII of human origin: human cell line and manufacturing characteristics. Eur J Haematol. 2012; 89(2):165-76.
Cataldi et al., Carbohydrate analysis by high performance anion-exchange chromatography with pulsed amperometric detection: the potential is still growing, Fresenius J Anal Chem, 2000; 368(8):739-58.
Collins et al., Factor VIII brand and the incidence of factor VIII inhibitors in previously untreated UK children with severe haemophilia A, 2000-2011. Blood. 2014; 124(23):3389-97.
Fang et al., The protein structure and effect of Factor VIII, Thrombosis Research, 2007; 119:1-13.
Fay, Factor VIII Function and structure, International Journal of Hematology, 2006; 83(2):103-108.
Girma et al., Assay of Factor VIII antigen (FVIII:CAg) in 294 Haemophilia A patients by a new commercial ELISA using monoclonal antibodies, Haemophilia, 1998; 4(2):98-103.
Grillo et al., Conformational origin of the aggregation of recombinant human Factor VIII, Biochemistry, 2001; 40:586-595.
Kelley et al., Development and validation of ab affinity chromatography step using a peptide ligand for cGMP production of Factor VIII, Biotechnology and Bioengineering, 2004; 87(3):400-12.
Kusch et al., Factor VIII assay mimicking in vivo coagulation conditions, Haemophilia, 2013; 20(2).
Lin et al., Relationship between Factor VIII:Ag and Factor VIII in recombinant and plasma derived Factor VIII concentrate, Haemophilia, 2004; 10:459-469.

(Continued)

*Primary Examiner* — Marsha Tsay
(74) *Attorney, Agent, or Firm* — Venable LLP; Keith G. Haddaway

(57) ABSTRACT

A process for manufacturing of a Factor VIII product having a ratio of FVIII:C/FVIII:Ag of at least 0.7 in the Factor VIII product by using chromatography wherein at least one chromatographic step is performed by means of employing; An affinity chromatography resin having an affinity for specifically binding of Factor VIII which is effected by an affinity ligand which is immobilised on the affinity chromatography resin, said affinity ligand is a 13 kD yeast derived Fab antibody fragment directed to the Factor VIII molecule. An anionic chromatography resin. A size exclusion resin. A Factor VIII product obtainable according to the process with a monomer content of >98% for treatment of haemophilia and avoiding formation of inhibitors.

15 Claims, 20 Drawing Sheets

(56) References Cited

OTHER PUBLICATIONS

Mire-Sluis et al., Analysis and immunogenic potential of aggregates and particles, Bioprocess International, Dec. 2011; 9(11):38-43.

Muyldermans, Single domain camel antibodies: current status, J. Biotechnol. 2001; 74(4):277-302.

Peerlinck et al., Factor VIII inhibitors in previous treated Haemophilia A patients with a double virus inactivated plasma derived Factor VIII concentrate, Thrombosis and Haemostasis, 1997; 77(1):80-86.

Rosen, Assay of Factor VIII:C with a chromogenic substrate, Scand J Haemetol Suppl., 1984; 33(540):139-145.

Sommer et al., Comparative field study evaluating activity of recombinant FVIII Fc fusion protein in plasma samples at clinical haemostatis laboratories, Heamophilia, 2013; 20(2)294-300.

Svensson et al., Evaluation of the metal binding site in a recombinant coagulation factor VIII identifies two sites with unique metal binding sites, Biological Chemistry, 2013; 394(6):761-65.

Wakabayashi et al., Metal ion-independent association of Factor VIII subunits and the roles of calcium and copper ions for cofactor activity and inter-subunit affinity, Biochemistry, 2001; 40(34):10293-10300.

Wang et al., Coagulation Factor VIII: structure and stability, International Journal of Pharmaceutics, 2003; 259:1-15.

Wang et al., Correlation with rFVIII inactivation with aggregation in solution, Pharmaceutical Research, 2003; 20(4):693-700.

McCue et al., Application of a novel affinity adsorbent for the capture and purification of recombinant Factor VIII compounds. Journal of Chromatography A. Sep. 23, 2009; 1216: 7824-30.

Thim et al., Purification and characterization of a new recombinant factor VIII (N8). Haemophilia. 2010; 16:349-59.

Cheng et al., Purification of coagulation factor VIII using chromatographic methods. Direct chromatography of plasma in anion exchange resins. Biotechnol. Lett. 2010; 32:1207-14.

Rotblat et al., Purification of human factor VIII:C and its characterization by western blotting using monoclonal antibodies. Biochemistry. 1985; 24:4294-4300.

Ge Healthcare, VIII Select, Feb. 2009 (2 pages), accessed at https://www.gelifesciences.com/gehcls_images/GELS/Related%20Content/Files/1314774443672/litdoc28966237AB_20110831120139.pdf.

Peak Results

| | Name | RT | Area | Height | % Area |
|---|---|---|---|---|---|
| 1 | | 32,595 | 12485306608 | 55110837 | 0,68 |
| 2 | Aggregates | 43,000 | | | |
| 3 | Monomer | 47,603 | 1787884705383 | 7152198232 | 97,21 |
| 4 | Fragments | 58,333 | 38908497096 | 171225327 | 2,12 |

Peak Results

| | Name | RT | Area | Height | % Area |
|---|---|---|---|---|---|
| 1 | Aggregates | 43,000 | | | |
| 2 | Monomer | 47,633 | 1893442741446 | 9902048058 | 98,50 |
| 3 | Fragments | 52,617 | 28802684958 | 192960787 | 1,50 |

Peak Results

|   | Name | RT | Area | Height | % Area |
|---|------|----|------|--------|--------|
| 1 | Aggregates | 43,000 | | | |
| 2 | Monomer | 47,499 | 1773602574318 | 9231478934 | 98,96 |
| 3 | Fragments | 54,628 | 18594141020 | 99103234 | 1,04 |

Peak Results

|   | Name | RT | Area | Height | % Area |
|---|---|---|---|---|---|
| 1 | Aggregates | 43,000 | | | |
| 2 | Monomer | 47,462 | 1723203354445 | 8844566443 | 98,63 |
| 3 | Fragments | 54,513 | 23977018029 | 123642477 | 1,37 |

Peak Results

| | Name | RT | Area | Height | % Area |
|---|---|---|---|---|---|
| 1 | Aggregates | 43,000 | | | |
| 2 | Monomer | 47,777 | 1960828944611 | 10028945141 | 98,72 |
| 3 | Fragments | 54,862 | 25412047468 | 133330008 | 1,28 |

PROCESS FOR MANUFACTURING FACTOR VIII HAVING AN IMPROVED RATIO OF FVIII:C/FVIII/AG

CROSS-REFERENCE TO RELATED APPLICATIONS

This application is a U.S. National Phase of International Application No. PCT/EP2015/051028, filed Jan. 20, 2015, which claims priority to European Application No. 141517693.8, filed Jan. 20, 2014, the entire contents of each are incorporated by reference herein.

The present invention pertains to a process for manufacturing of a Factor VIII product having an improved ratio of FVIII:C/FVIII:Ag in the Factor VIII product by using chromatography and a medicament comprising the product obtainable by the process of the invention with a monomer content of ≥98%.

BACKGROUND OF THE INVENTION

The native Factor VIII molecule is under normal conditions circulating in a complex having a light (for both full length plasma derived and B-domain deleted FVIII; 80 kDa) and a heavy chain (for plasma or recombinant full length derived Factor VIII 200 kDa and for B-domain deleted recombinant Factor VIII 90 kDa). The exact conditions of the heavy and the light chain association are not in detail known, but articles suggest the involvement of a metal ion bridge which together with hydrophobic interactions is forming and holding together the complex. Different metal ions have been suggested to take part in the interaction, including calcium, copper, zinc, manganese etc.[1] For a recently developed B-domain deleted recombinant Factor VIII product, it was stated that the molecule contained three metal ions; calcium, copper and zinc.[2] Without the metal bridge the light and heavy chain of the Factor VIII molecule alone, have no biological activity but still antigen activity. It has been published in several publications[3,4] that there is an in vivo risk of inhibitor formation especially towards the Factor VIII light chain. Thus, in the Factor VIII product injected in patients, as low amounts of single light and heavy chain as possible should be present, the ratio of FVIII:C/FVIII:Ag activity should be close to 1.0 (one)[5], especially in respect of Factor VIII light chain.

In general, protein aggregation is a risk factor in a purification process not only because of losses of the desired product but also in regard of potential inhibitor formation[6]. Under certain biochemical conditions recombinant Factor VIII may aggregate[7,8] which will result in a significant reduction of its biological activity. A Factor VIII product with aggregated Factor VIII will thus contain inactive forms of Factor VIII with a monomer content <100%. The monomer content of a pharmaceutical protein product should be close to 100% with as low as possible an amount of inactive forms of Factor VIII (aggregates, fragments etc.).

Many processes have been described for purification of Factor VIII from plasma or cultures which recombinantly produce Factor VIII (rFVIII). As an example WO 2009/156430 discloses a series of chromatographic steps for purification of Factor VIII, including a non animal derived Fab based affinity step where the 13 kDalton ligand binds to the light chain of Factor VIII. Other chromatography steps mentioned in the application includes anion and cation mixed mode resins, cation exchange, anion exchange and gel filtration. No information in regard of removal of inactive forms or content of aggregate of Factor VIII is provided in this patent application. In the article; Purification and characterization of a new recombinant factor VIII[9] a four step chromatographic purification process of Factor VIII is described including an affinity step with a monoclonal antibody as ligand which binds to the heavy chain of Factor VIII. The other three steps are a mixed mode chromatography resin, an anion exchange resin and a gel filtration step, no information in regard of removal of inactive forms or content of aggregate of Factor VIII is provided in this article. In the article; Development and validation of an affinity chromatography step using a peptide ligand for cGMP production of Factor VIII[10], a five step chromatography method is described including a peptide based affinity step where the 2.7 kDalton ligand binds to the light chain of Factor VIII. It is described that excess of Factor VIII light chain from the cultivation process is removed during wash of the peptide affinity resin. The other four chromatography steps are cation exchange resin, anion exchange resin, hydrophobic interaction resin and a gel filtration step. It is stated that two chromatographic steps following the peptide affinity resin removes excess of Factor VIII light chain, but not further defined in which of the steps. No information in regard of removal of other inactive forms than Factor VIII light chain or content of aggregate of Factor VIII is provided in this article. In the article; application for a novel affinity adsorbent for the capture and purification of recombinant Factor VIII compounds[11], a Fab based 13 kDalton ligand affinity resin is described for purification of Factor VIII, no information in regard of removal of inactive forms or content of aggregate of Factor VIII is provided in this article.

As described in the articles[5],[12], commercially available recombinant Factor VIII products on the market contain inactive Factor VIII forms, as measured with the ratio of biologically active Factor VIII (Factor VIII:C) related to the total amount of Factor VIII (Factor VIII:Ag), with a potential of negative effects for the patients in regard of immunological reactions.

Biologically active Factor VIII is defined as Factor VIII having Factor VIII activity which under normal conditions in vivo can be activated to Factor VIIIa through enzymatic reactions, which is an essential part of the coagulation cascade with the aim to stop bleedings. Biologically active Factor VIII can be measured with different in vitro analytical methods (FVIII:C), for example FVIII chromogenic assay and/or one stage clot assay.[13] The chromogenic assay is a two-stage photometric method that measures the biological activity of factor VIII as a cofactor. Factor VIII activates factor X into factor Xa, which in turn is enzymatically cleaved into a product that can be quantified spectrophotometrically. The one-stage clotting assay is based on the ability of a factor VIII containing sample to correct the coagulation time of factor VIII deficient plasma in the presence of phospholipid, contact activator and calcium ions. The time of appearance of a fibrin clot is measured in one step.

WO-A-2008/134310 discloses a method for stabilizing a bulk solution of recombinant protein for frozen storage, which comprises providing a partially-purified solution of recombinant protein which has a monovalent salt concentration of at least 100 mM, and adding a carbohydrate to said solution in an amount sufficient that, upon freezing, the solution has a glass transition temperature of −56° C. or higher.

WO 2010/115866A1 discloses molecules and polypeptides comprising at least one amino acid sequence having significant identity with (homology to) human Factor VIII or biologically active portion(s) thereof, related molecules (such as nucleic acids encoding such polypeptides), compositions (such as pharmaceutical formulations) comprising such polypeptides, and methods of making and using such polypeptides.

WO 97/33178A1 discloses a process for testing the suitability of protein fractions containing factor VIII, further processing of which involves a pasteurization stage, involves testing the starting material for fragments in the 20-50 kD range. Factor VIII fragments in this range obviously give rise to inhibitor formations in patients previously treated with factor VIII. Even batches contaminated with these fragments can be used to produce very pure virus-free factor VIII by applying size exclusion chromatography on hydrophilic materials.

U.S. Pat. No. 4,675,385 A discloses a rapid and simple process for purifying human, bovine and porcine procoagulant protein Factor VIII on a large scale using sequential high performance size exclusion chromatography under, first, low salt concentration conditions and, second, under high salt concentration conditions from reconstituted commercial Factor VIII:C (complexed Factor VIII) concentrate. The chromatographic separation is carried out on a high performance size exclusion chromatographic column packed with porous beads having a particle size of from about 13 to about 35 microns, pore diameters of from about 500 to about 2000 Angstroms and a pore volume of from about 1.0 to about 1.8 ml per gram. The first chromatographic separation is carried in a buffered aqueous solution using the buffered aqueous solution as an eluant. The low molecular weight constituents (impurities) are separated from Factor VIII and the high molecular weight constituents (impurities). A second chromatographic separation may be carried out after Factor VIII has been dissociated in a buffered solution having a concentration of from about 0.25 to about 0.45M calcium ion. The second chromatographic column is packed with some packing as the first column and is eluted with a buffered aqueous solution containing 0.25 to 0.45M calcium ion. In a column of 2.5×60 cm, 4 gms of commercial Factor VIII concentrate can be purified in less than two hours. The process is amenable to scale up.

EP 0 412 466 A2 discloses a process for the preparation of a pasteurized factor VIII concentrate with high specific activity and stability is described and comprises impurities being adsorbed from the solution containing factor VIII by at least two adsorptions using $Al(OH)_3$, an anion exchanger or $Ca_3(PO4)_2$, preferably using two different adsorbents from this group.

FR 2 650 393 A1 discloses obtaining a factor VIII concentrate having a specific activity and a high yield, which concentrate is free of foreign protein of non-human origin. Factor VIII obtained by any process is deposited on a column containing an anion exchange gel preequilibrated with a first buffer. After having charged the factor VIII onto the column, the gel is washed with a second buffer until an optical density less than 0.1 is obtained. The purified factor VIII is then released from the gel with a 3rd buffer. After chromatography, the specific activity is 30/1600 IU/mg.

Cheng, Elisabeth et al., discloses in Biotechnology Letters, v.32, n.9, p.1207-1214, 2010, that human FVIII was purified directly from plasma using anion exchange chromatography followed by gel filtration. Three Q-Sepharose resins were tested, resulting in 40% recovery of FVIII activity using Q-Sepharose XL resin, about 80% using Q-Sepharose Fast Flow and 70% using the Q-Sepharose Big Beads. The vitamin K-dependent coagulation factors co-eluted with FVIII from the anion exchange columns. In the second step of purification, when Sepharose 6FF was used, 70% of FVIII activity was recovered free from vitamin K-dependent factors.

BRIEF DESCRIPTION OF THE INVENTION

An object of the invention is to provide a process to reduce the amount of single light and heavy chain in a process of manufacturing of Factor VIII and providing a product of high monomer content, for in particular recombinantly produced Factor VIII. Another object of the invention is to provide a composition in which single light and heavy chain (fragments) and aggregated Factor VIII forms can be removed and that the resulting essential monomeric Factor VIII solution can be stored in frozen and/or freeze-dried state for several years, keeping its high monomeric Factor VIII content.

Surprisingly it has been found by the inventors of the present invention that a process for manufacturing of a Factor VIII product, having a ratio of FVIII:C/FVIII:Ag of at least 0.7 and a high monomer content in the Factor VIII product by using chromatography, is able to solve the object underlying the invention. The process of the invention comprises a performance wherein at least one chromatographic step is performed by means of employing an affinity chromatography resin having an affinity for specifically binding of Factor VIII which is effected by an affinity ligand which is immobilised on the affinity chromatography resin, said affinity ligand is a 13 kD yeast derived Fab antibody fragment directed to the Factor VIII molecule.

Said affinity ligand binds to the light chain part of the FVIII molecule. Surprisingly, in a solution comprising a mixture containing native Factor VIII formed by the light and heavy chain of Factor VIII in complex and the single light FVIII chain without any biological FVIII activity, the FVIII light chain without any biological coagulation activity could be removed from the mixture by processing over said affinity resin by employing specific washing conditions. The skilled person would expect, that also a significant amount of the native Factor VIII molecule, i.e. complex of heavy and light chain is removed.

Said ligand is in particular immobilised on an affinity chromatography resin via a hydrophilic spacer arm, which resin is a cross-linked agarose base matix, said affinity ligand is a 13 kD yeast derived Fab antibody fragment directed to the Factor VIII molecule, and commercially available from GE Healthcare under the trade name VIIISelect.

Alternatively the object is achieved by a process for providing a ratio of FVIII:C/FVIII:Ag of at least 0.7 and resulting in a high Factor VIII monomer content wherein at least one chromatographic step is performed by means of employing at least one chromatographic step on an anion exchange chromatography resin.

In another alternative of the present invention a process for providing a ratio of FVIII:C/FVIII:Ag of at least 0.7 and a high Factor VIII monomer content is disclosed wherein at least one chromatographic step is performed by means of employing a size exclusion chromatography step under specific chromatography conditions and buffer composition.

In another alternative of the invention, using the same chromatography steps as for the FVIII:C/FVIII:Ag removal, the monomer content after Factor VIII product is ≥98%.

In an additional alternative of the invention, the resulting high FVIII:C/FVIII:Ag ratio and high FVIII: monomer content from a previous chromatography step can be stored for at least 12 months, preferable for at least 24 months and most preferable for at least 36 months in frozen and/or freeze-dried state, with unchanged properties of FVIII:C/FVIII:Ag and/or a high Factor VIII monomer content, until used by a patient.

If two methods of the three methods of the invention are combined it is possible to achieve a ratio of FVIII:C/FVIII:Ag of at least 0.8 and if all three are combined, then a ratio of at least 0.9 becomes possible.

For example the process of the present invention is represented by a process for manufacturing of a Factor VIII product, having a ratio of FVIII:C/FVIII:Ag of at least 0.7 and giving a high Factor VIII monomer content of ≥98% and essential no aggregated Factor VIII product by using chromatography, wherein step (a) at least one chromatographic step is performed by means of employing an affinity chromatography resin having an affinity for specifically binding of Factor VIII which is effected by an affinity ligand which is immobilised on the affinity chromatography resin, said affinity ligand is a 13 kD yeast derived Fab antibody fragment directed to the Factor VIII molecule with the process of the invention, and wherein step (b) at least one chromatographic step on an anion exchange chromatography resin is performed. The order of steps may be (b) after (a) or (a) after (b).

According to the invention it is also possible to perform the following process for manufacturing of a Factor VIII product, having a ratio of FVIII:C/FVIII:Ag of at least 0.7 and giving a high Factor VIII monomer content of ≥98% and essential no aggregated Factor VIII product by using chromatography, wherein step (a) at least one chromatographic step is performed by means of employing an affinity chromatography resin having an affinity for specifically binding of Factor VIII which is effected by an affinity ligand which is immobilised on the affinity chromatography resin, said affinity ligand is a 13 kD yeast derived Fab antibody fragment directed to the Factor VIII molecule with the process of the invention, and wherein step (c) at least one chromatographic step is performed by means of employing a size exclusion chromatography step. The order of steps may be (c) after (a) or (a) after (c).

According to the invention it is also possible to perform the following process for manufacturing of a Factor VIII product, having a ratio of FVIII:C/FVIII:Ag of at least 0.7 and giving a high Factor VIII monomer content of ≥98% and essential no aggregated Factor VIII product by using chromatography, wherein step (b) at least one chromatographic step on an anion exchange chromatography resin is performed and wherein step (c) at least one chromatographic step is performed by means of employing a size exclusion chromatography step. The order of steps may be (c) after (b) or (b) after (c).

A still further embodiment is the combination of the three processes of the invention. For example the process of the present invention is then represented by a process for manufacturing of a Factor VIII product, having a ratio of FVIII:C/FVIII:Ag of at least 0.9 and giving a high Factor VIII monomer content of ≥99% and essential no aggregated Factor VIII product by using chromatography, wherein step (a) at least one chromatographic step is performed by means of employing an affinity chromatography resin having an affinity for specifically binding of Factor VIII which is effected by an affinity ligand which is immobilised on the affinity chromatography resin, said affinity ligand is a 13 kD yeast derived Fab antibody fragment directed to the Factor VIII molecule with the process of the invention, and wherein step (b) at least one chromatographic step on an anion exchange chromatography resin is performed, and wherein step (c) at least one chromatographic step is performed by means of employing a size exclusion chromatography step. The order of steps may be (a), (b), (c); (a), (c), (b); (c), (b), (a); (c), (a), (b); (b), (c), (a); (b), (a), (c).

According to the invention, the Factor VIII molecule used in the processes of the invention is a complex of a light chain and a heavy chain and the improved ratio of FVIII:C/FVIII:Ag results from depletion of the Factor VIII light chain, the Factor VIII heavy chain and/or dissociated Factor VIII light chain/Factor VIII heavy chain from the complex. The dissociated Factor VIII chains can either be present originating from the culture production process due to mutations, proteolytic/physical degeneration etc., or due to enzymatical/physical degeneration during a purification process. Dissociated FVIII light and/or FVIII heavy chain will form either Factor VIII fragments and/or Factor VIII aggregates depending on environment e.g. buffer, protein concentration etc. It is thus advantageous to remove all forms of Factor VIII which are not monomeric and/or possess a potential to form aggregates easier than the native form of Factor VIII.

According to another aspect of the invention, the Factor VIII molecule used in the process could be non-covalently and/or covalently bound to other substances for example, vWF, PEG, HES and or $F_c$ fragments of antibodies etc. for improving half life prolongation of the Factor VIII product, arriving at the same solution of the invention with high ratio of biological activity and high monomer content of the final product.

In a particular embodiment of the invention the affinity chromatographic step is performed under conditions providing for binding of Factor VIII to the affinity resin and removing the dissociated light chain by washing off, before Factor VIII is eluted. Binding of the Factor VIII to the affinity chromatography resin occurs under low salt conditions equivalent to a concentration of about 0.1-about 0.5 mol/kg sodium chloride. Then a washing of the affinity chromatography resin under increased salt concentration equivalent to in the range of about 0.3-about 4 mol/kg sodium chloride is performed for removal of the light chain, and thereafter optionally an eluting and collecting step is performed to obtain Factor VIII in a separate fraction by employing a salt concentration equivalent to in the range of about 0.5-about 4 mol/kg sodium chloride and/or $MgCl_2$ in combination with about 40-about 60% of an alcohol, preferable ethylene glycol or propylene glycol or mixtures thereof.

The affinity resin has been designed for binding the light chain rather than other portions of the Factor VIII molecule. This was enabled by using an affinity ligand of a specific size. It is known that affinity ligands which are too small, for example chemical synthesised molecules, due to sterically hindrance sometimes have difficulties binding to the target protein. Therefore the size of the affinity ligand required for the invention is in the range of ≥10 kDalton. As the strong affinity expected for a Fab fragment molecule of this size[14] and that the ligand is directed against the FVIII light chain, in fact, therefore it was surprising that the FVIII light chain could be washed off before eluting the native complex containing the FVIII heavy chain together with FVIII light chain. In particular, the affinity resin is based on a cross linked agarose matrix with an average particle size of about 74 µm and that the about 13 kD yeast derived $F_{ab}$ antibody fragment affinity ligand, is bound to the matrix through a hydrophilic spacer arm to make the ligand more available for binding to the Factor VIII molecule. The affinity ligand binds to the Factor VIII light chain of the biologically active Factor VIII molecule.

In another embodiment of the process of the invention the affinity chromatographic conditions comprise at least two of the following conditions;

- a resin load of biologically active Factor VIII of at least 5,000 IU/mL resin, preferably at least 10,000 IU/ml resin and most preferably more than 20,000 IU/mL resin.
- Buffer conditions during Factor VIII load: about 0.1-about 0.5 mol/kg NaCl, about 0.01-about 0.05 mol/kg $CaCl_2$, about 0.01-about 0.05 mol/kg L-histidine, about 0.005-about 0.05% (w/w) Polysorbate 80, about 0.5-about 2% Triton X-100, about 0.1-about 1% TNBP at pH 6.2-6.8
- Buffer conditions during wash: about 0.5-about 4 mol/kg NaCl, about 0.01-about 0.05 mol/kg $CaCl_2$, about 0.01-about 0.05 mol/kg L-histidine, about 0.005-about 0.05% (w/w) Polysorbate 80 at pH 6.2-6.8
- Buffer condition during elution of Factor VIII: about 0.5-about 4 mol/kg NaCl, about 40-about 60% ethylene glycol, about 0.01-about 0.05 mol/kg $CaCl_2$, about 0.01-about 0.05 mol/kg L-histidine, about 0.005-about 0.05% (w/w) Polysorbate 80 at pH 6.2-6.8.

In another particular embodiment of the process of the invention the anion exchange chromatography is performed under conditions providing a binding of Factor VIII to the anion exchange chromatography resin and the biologically inactive forms are removed from the anion exchange chromatography resin either before or after elution of biologically active Factor VIII. The Factor VIII monomer content in the elution fraction is ≥98%. According to the process of the invention Factor VIII is loaded under low salt conditions equivalent to a concentration of 0.01-0.15 mol/kg sodium chloride for binding of Factor VIII and inactive forms of Factor VIII are removed, the anion exchange chromatography resin is washed under medium salt conditions equivalent to a concentration of 0.15-0.3 mol/kg sodium chloride for removal of inactive forms of Factor VIII, and Factor VIII is eluted from the anion exchange chromatography resin and collected in a separate fraction by employing high salt conditions equivalent to a concentration of 0.3-1 mol/kg sodium chloride.

Further inactive Factor VIII forms are eluted from the anion exchange chromatography resin and collected in a separate fraction by employing high salt conditions equivalent to a concentration of 1-2 mol/kg sodium chloride.

In a particular embodiment of the anion exchange process of the invention, the biologically inactive Factor VIII is removed through the anion exchange chromatography step, resulting in a monomer content of ≥98% in the product elution fraction, comprising at least two of the following chromatographic conditions:

- a resin load of biologically active Factor VIII of at least 10,000 IU/mL resin, preferably at least 15,000 IU/ml resin and most preferably more than 20,000 IU/mL resin;
- Buffer conditions during Factor VIII load: about 0.05-about 0.15 mol/kg NaCl, about 0.01-about 0.05 mol/kg $CaCl_2$, about 0.01-about 0.05 mol/kg L-histidine, about 0.005-about 0.05% (w/w) Polysorbate 80 at pH 6.0-7.5;
- Buffer conditions during wash: about 0.15-about 0.3 mol/kg NaCl, about 0.01-about 0.05 mol/kg $CaCl_2$, about 0.01-about 0.05 mol/kg L-histidine, about 0.005-about 0.05% (w/w) Polysorbate 80 at pH 6.0-7.5;
- Buffer conditions during Factor VIII elution; about 0.3-about 0.5 mol/kg NaCl, about 0.01-about 0.05 mol/kg $CaCl_2$, about 0.01-about 0.05 mol/kg L-histidine, about 0.005-about 0.05% (w/w) Polysorbate 80 at pH 6.0-7.5.

In a further embodiment of the anion chromatography process of the invention, the anion exchange resin is a strong anion exchanger with a quaternary ammonium ion as ligand coupled to a cross-linked 6% agarose matrix with a spherical diameter of about 45-about 165 µm, with a total ion binding capacity of about 0.18-about 0.25 mmol/mL.

In another particular embodiment of the process of the invention the size exclusion chromatography comprises at least two of the following chromatographic conditions:

- a sample load of about 4-about 8% of the column volume,
- a column height of about 60-about 90 cm,
- a biologically active Factor VIII concentration in the sample load of at least 10,000 IU/mL, preferably at least 15,000 IU/ml and most preferably more than 20,000 IU/mL,
- a column equilibration buffer for aggregation of inactive forms of Factor VIII; about 0.2-about 0.7 mol/kg NaCl, about 0.01-about 0.05 mol/kg $CaCl_2$, about 0.01-about 0.05 mol/kg Sodium citrate, about 0.5-about 2% (w/w) sucrose, about 0.5-about 2% (w/w) L-arginine, about 0.1-about 1% (w/w) Poloxamer 188 at pH 6.0-7.5,
- wherein the biologically active Factor VIII is collected in the monomeric form, whereas inactive Factor VIII is found either in the fraction containing aggregated inactive forms (could be both aggregated fragments (inactive) and aggregated monomeric Factor VIII (active when monomer but partly inactive when aggregated)) of a size exclusion chromatography step and/or in the fraction containing fragmented forms of Factor VIII of a size exclusion chromatography step and
- Factor VIII monomer collection is starting when about 30-about 40 mAU absorbance peak is recorded at the outlet of the column and stopped when absorbance peak is reverting back to about 1-about 40 mAU, relating to 2-3 times the amount of sample application.

In a particular embodiment of the size exclusion chromatography of the invention the size exclusion resin is a spherical crosslinked Agarose/Dextran media with a mean diameter of about 34 µm and an optimal separation range between 10,000-600,000 Dalton.

In another particular embodiment of the process of the invention the size exclusion chromatography eluate is stable for at least 12 months, in particular 36 months comprises at least two of the following conditions:

- A buffer composition comprising; about 0.2-about 0.7 mol/kg NaCl, about 0.01-about 0.05 mol/kg $CaCl_2$, about 0.01-about 0.05 mol/kg Sodium citrate, about 0.5-about 2% (w/w) sucrose, about 0.5-about 2% (w/w) L-arginine, about 0.1-about 1% (w/w) Poloxamer 188 at pH 6.0-7.5,
- A frozen solution stored at −60° C.,
- The freezing of the solution from room temperature until −40° C. is accomplished 90 minutes.
- The frozen solution according to storage at −60° C., is thawed to 18-25° C. at ≤90 minutes.
- The thawed solution is applied to a freeze drying process after adjustment of Factor VIII concentration with above mentioned buffer and filled in glass vials at 250 IU, 500 IU, 1000 IU, 2000 IU, 3000 IU, 4000 IU or 5000 IU Factor VIII per vial.
- The freeze dried product according to above where the Factor VIII monomer content is ≥99%.
- The freeze dried product according to above that can be stored at least 12 months, preferably 24 months and most preferably 36 months, without significantly change in the Factor VIII monomer after reconstitution and use by the patient.

The reconstituted product of above that has a buffer composition of; about 0.2-about 0.7 mol/kg NaCl, about 0.01-about 0.05 mol/kg CaCl$_2$, about 0.01-about 0.05 mol/kg Sodium citrate, about 0.5-about 2% (w/w) sucrose, about 0.5-about 2% (w/w) L-arginine, about 0.1-about 1% (w/w) Poloxamer 188 at pH 6.0-7.5

Subject matter of the present invention is also a Factor VIII product obtainable according to the method of the invention for treatment of haemophilia and avoiding formation of inhibitors which product is stable in frozen and/or freeze dried condition for at least 6 months, preferably for at least 12 months, more preferably for at least 24 months and most preferably up to 36 months. This Factor VIII is obtainable by the particular process of passing the above described three purification steps, 1. affinity step, 2. anion exchange step, 3. size exclusion chromatography step in that order.

By providing this order of purification scheme the resulting FVIII product quality in regard of high FVIII C/Ag ratio and high monomer content (equal to low aggregate and fragments) was compared to recombinant FVIII products on the market using different purification schemes[22]. The Factor VIII product of the present invention showed superior results in regard to high ratio Factor VIII C/Ag and high monomer and low fragment content, as can be seen in Table 1. In a further comparison in vivo between the product of the invention and one recombinant product on the market, reduced amounts of inhibitor incidents in previous untreated haemophilia A patients could be noticed, as can be seen in Table 2. The rFVIII product using the purification method A [22] of Table 2 does not have the same high capability to increase the FVIII C/Ag ratio and to reveal a product with high monomeric and low fragment content, as the purification method of the invention, which apparently affects the amount of immunological incidents in previously untreated haemophilia A patients.

TABLE 1

|  | FVIII/vial, IU | FVIII:C, IU/mL | FVIII:Ag, IU/mL | C/Ag | SEC-HPLC2, % | | |
|---|---|---|---|---|---|---|---|
|  |  |  |  |  | Aggregate | Monomer | Fragment |
| rFVIII acc. to pur. meth. A | 250 | 95 | 132 | 0.72 | 0 | 76 | 24 |
| rFVIII acc. to pur. meth. A | 1000 | 441 | 573 | 0.77 | 0 | 76 | 24 |
| rFVIII acc. to pur. meth. A | 3000 | 638 | 925 | 0.69 | 0 | 76 | 24 |
| rFVIII acc. to pur. meth. B | 1000 | 242 | 263 | 0.92 | 0 | 99 | 1 |
| rFVIII acc. to pur. meth. C | 500 | 104 | 130 | 0.8 | 0 | 77 | 23 |
| rFVIII acc. to pur. meth. C | 1000 | 205 | 270 | 0.76 | 0 | 80 | 20 |
| rFVIII acc. to pur. meth. C | 3000 | 600 | 732 | 0.82 | 0 | 77 | 23 |
| rFVIII acc. to pur. met. of inv. | 250 | 119 | 131 | 0.91 | 0 | 100 | 0 |
| rFVIII acc. to pur. met. of inv. | 1000 | 494 | 531 | 0.93 | 0 | 100 | 0 |

TABLE 2

|  | FVIII/vial, IU | FVIII:C, IU/mL | FVIII:Ag, IU/mL | C/Ag | SEC-HPLC2, % | | | Previously untreated patients (PUP's) Inhibitors, % (n = amount of patients) |
|---|---|---|---|---|---|---|---|---|
|  |  |  |  |  | Aggregate | Monomer | Fragment |  |
| rFVIII acc. to pur. meth. A | 250 | 95 | 132 | 0.72 | 0 | 76 | 24 | 35.2 (128)* |
| rFVIII acc. to pur. meth. A | 1000 | 441 | 573 | 0.77 | 0 | 76 | 24 |  |
| rFVIII acc. to pur. meth. A | 3000 | 638 | 925 | 0.69 | 0 | 76 | 24 |  |
| rFVIII acc. to invention | 250 | 119 | 131 | 0.91 | 0 | 100 | 0 | 11.6 (43)** |
| rFVIII acc. to invention | 1000 | 494 | 531 | 0.93 | 0 | 100 | 0 |  |

*Published studyCollins2014[21],
**On-going study

Another subject matter of the present invention is the improved product performance of the present invention in comparison with EP2537862A1. This is especially achieved by the particular process of passing the above described three purification steps, 1. affinity step, 2. anion exchange step, 3. size exclusion chromatography step in that order. In addition comprising the specific process conditions of the size exclusion steps of the invention which secure the demanded high (>0.9) Factor VIII C/Ag ratio and monomer content (>99%) in the patients. This is achieved also after storage at −70° C. for 12 months when the Factor VIII is stored by using the specific buffer conditions of the invention which are provided by the last size exclusion buffer exchange step and freeze-drying of the product. This seems to minimize unfavourable Factor VIII C/Ag ratio and a decrease in monomer content during the storage period, which ensures that the product given to the patients has a reduced risk for unwanted immunological reactions due to aggregate/fragment in the solution which is injected in the patients (after reconstitution of the stored freeze-dried product). Furthermore, the specific activity as measured with FVIII:C/protein concentration using the Bradford analytical method is statistical significantly higher (10000 IU/mg, n=9) compared to the value disclosed in EP2537862A1 (8061 IU/mg, n=1). The specific activity is an indication of purity of the FVIII product (different protein measurement method is known to give different results, thus same protein method is needed for comparable values) indicating the superior performance of the product of the invention compared to EP2537862A1, as protein impurities is one of risk factor for inhibitor incidents in patients. In addition, the protein fingerprinting analysis by isoelectric focusing as revealed in EP2537862A1 and can be found in FIG. 17 in the invention indicates the difference in product properties of respectively product.

In a particular embodiment of the invention the Factor VIII is characterised in that the quotient of biologically active Factor VIII (FVIII:C) in relation to the total amount of Factor VIII (FVIII:Ag) is ≥0.7, preferably ≥0.8, more preferably ≥0.9 and most preferably 1, and the Factor VIII monomer content is ≥98%, preferably, ≥99% and most preferably 100% after the last step and that essential no aggregated Factor VIII can be detected.

In another embodiment of the invention the Factor VIII is keeping its biological activity, high content of monomeric Factor VIII and low aggregated/fragmented Factor VIII content.

In still another embodiment the Factor VIII of the invention is characterized in that it is plasma derived, recombinant derived and/or a deletion derivate or a truncated form of Factor VIII with biological activity, in particular a B domain deleted FVIII, such as described in [20], incorporated by reference.

In yet another embodiment of the invention the Factor VIII is characterized that in case it is recombinantly derived and/or a deletion derivate it is produced in human cells.

In a particular embodiment of the invention the Factor VIII is characterised in that the amount of inhibitors in previous treated or untreated Haemophilia A patients treated with the product, is <25%, preferably <20%, more preferably <10% and preferably preferable 0%.

Subject matter of the invention is also a Factor VIII product obtainable according to the method of the invention for treatment of haemophilia and avoiding formation of inhibitors.

In particular, the product according to the invention shows an amount of inhibitors in previously treated or untreated Haemophilia A patients after treatment with the product of the invention of <about 25%, preferably <about 20%, more preferably <about 10% and most preferably about 0%.

Cryo-/lyoprotectants are recommended to protect the protein during the freeze-drying process and during storage, by forming an amorphous matrix surrounding the protein.

A bulking agent may be included to function as a cake former to give mechanical support during freeze-drying and to increase the dry weight of the drug product. The bulking agent thereby contributes to provide a uniform quality and appearance of a lyophilized product.

Furthermore, a buffering agent can be added to maintain the pH to a value suitable for the protein and for therapeutic use of the product. Suitable ingredients for lyophilized proteins are for example disclosed in WO2010/026186 A, incorporated by reference.

BRIEF DESCRIPTION OF THE DRAWINGS

FIG. 1 shows the removal of inactive FVIII:C in the flow through and wash fractions of the affinity step and the anion exchanger step. The wash fraction of the affinity step contains almost only FVIII light chain.

FIG. 2 shows the FVIII Western blot pattern at equal FVIII:C concentration after the affinity step, after the anion exchange step and after the size exclusion step, all showing the same pattern as the FVIII control.

Figure 1:
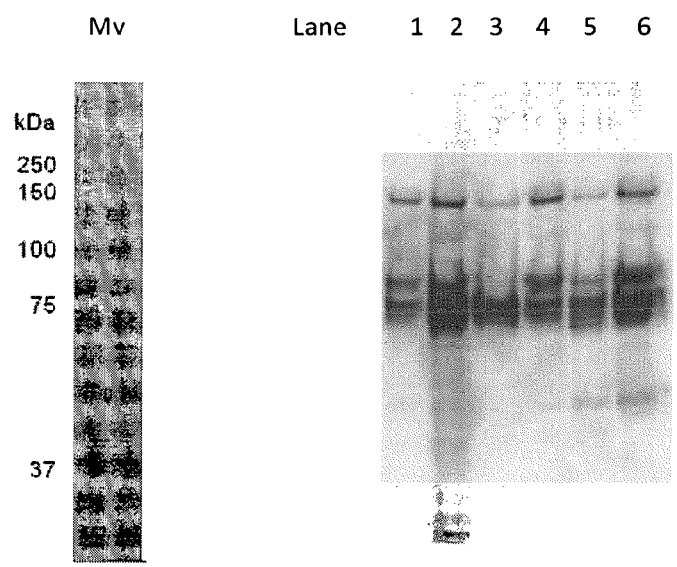
FIG. 1: Western blot using FVIII antibodies. From left molecular weight standard, Lane 1; Starting material affinity step, FVIII:Ag 5.0 IU/mL, Lane 2; flow through affinity step, FVIII:Ag 132 IU/ml, Lane 3; affinity wash fraction, FVIII:Ag 26 IU/ml, Lane 4; affinity eluate (starting material Q), FVIII:Ag 5.8 IU/ml, Lane 5; anion exchange flow through+ eq., FVIII:Ag 1.7 IU/ml, Lane 6; anion exchange wash, FVIII:Ag 5.0 IU/ml.

The term "biologically inactive Factor VIII form" according to the invention means a Factor VIII form that has lost its biological activity due to chemical, biochemical or enzymatic causes. Biologically inactive Factor VIII can for example be a single Factor VIII light or heavy chain, truncated form of Factor VIII or activated form (but unstable, as defined by activation in the coagulation cycle) of Factor VIII (such as FVIIIa) and/or aggregated or further forms of fragmented Factor VIII.

The definition of mol/kg used in the application is; amount of mol added to 1,000 g of water, the definition of Molar is: amount of mol added up to 1,000 mL of water.

The total amount of both biologically active and inactive Factor VIII in a sample is measured with an antigen based ELISA analytical method of (FVIII:Ag). The ratio between biologically active Factor VIII (FVIII:C) and antigen content of Factor VIII (FVIII:Ag) in a sample with full biological activity (as in vivo) should be equal to 1.0. If the ratio is smaller than 1, this is an indication that there are inactive forms of Factor VIII in the sample. Inactive forms could either be aggregated Factor VIII and/or a Factor VIII molecule which has dissociated in its single Factor VIII light and heavy chain.

FVIII light chain (A3, C1 and C2 domain of Factor VIII, with a molecular weight of approximately 80 kD) is, in the biologically active Factor VIII molecule, a metal/hydrophobic complex with the FVIII heavy chain (A1 and A2 Factor VIII domain, with a molecular weight of 90-210 kD). This complex is the native Factor VIII molecule in vivo which under normal conditions circulates bound to von Willebrandt Factor (vWF) which protects it from degeneration. When the coagulation system is activated, the native Factor VIII molecule is released from vWF and bound on activated platelets and converted proteolytical to FVIIIa (activated Factor VIII), which is the active form of the native FVIII molecule, an important part of the coagulation system. The FVIIIa molecule is consumed fast by the coagulation cascade and thereafter inactivated enzymatically by different protease inhibitors.[15] If the complex is dissociated[16], the light chain or the heavy chain have no or little biological activity and the ratio FVIII:C/FVIII:Ag is close to zero. If the native complex is proteolytical inactivated, the molecular weight of both the light and heavy chain will decrease, the Factor VIII degradation products have initially a remaining biological activity (for example FVIIIa) but they are unstable and will relatively fast be inactivated in vivo.[1] Factor VIII degradation products (both proteolytically degraded and non proteolytical dissociated) can be detected with the Factor VIII Western blot analytical method which specifically shows biologically active and inactive Factor VIII molecules based on size. The native Factor VIII molecule has a molecular weight of approximately 170 kDalton or 290 kDalton depending if the molecule is B-domain deleted or not. The B-domain has no biologically active function in the Factor VIII molecule, thus, a biologically active Factor VIII molecule can be either with or without the B-domain (or without part of it).

A Factor VIII monomeric product is defined herein as a biologically active Factor VIII molecule having the same molecular weight mass defined by an analytical HPLC size exclusion chromatography method performed under native buffer conditions. Fragmented Factor VIII forms are mainly inactive whereas aggregated Factor VIII forms have reduced biological activity. Both forms exert a theoretical increased risk of inhibitor formation in vivo and should be as low as possible in a Factor VIII product aimed for haemophilia A treatment. The monomeric Factor VIII product should be as high as possible at the end of the purification process and as well be stable before (frozen state) the pharmaceptical processing of the Factor VIII product and under the actual pharmaceptical processing (freeze-drying or filling liquid solution in vials) until reconstituted and consumed by the patients. This time period can often be from several months up to 1-3 years. One example of stability in frozen solution of Factor VIII is provided in U.S. Pat. No. 8,187,799 B2 where specific buffer compositions are claimed, however, Factor VIII aggregate/monomer content is not discussed in that reference.

The recombinant Factor VIII of the invention is in particular a deletion derivative fully or partially lacking the B-domain, thereby providing a specific activity which can vastly exceed 5,000 IU/mg in the final purified product. Examples of such deletion derivatives fully or partially lacking their B-domains are disclosed and prepared in EP-A-1136553 and EP-A-1739179 from human cell lines. It is appreciated that the presently invented compositions, as being described in the following section, are especially well suited to be applied to such deletion derivatives of Factor VIII or other Factor VIII products of similar high purity.

DETAILED DESCRIPTION OF THE INVENTION

Detailed Description of the Factor VIII Affinity Chromatography Step

Factor VIII is bound to the Factor VIII affinity chromatography column (VIIISelect) under equilibration buffer conditions (0.3 mol/kg NaCl, 0.02 mol/kg $CaCl_2$, 0.02 mol/kg L-histidine, 0.02% (w/w) Polysorbate 80, pH 6.4-6.6, conductivity 30-36 mS/cm) with or without solvent detergent chemicals (1% Triton X-100+0.3% tri-n butyl phosphate), which can be applied to the Factor VIII solution before the affinity step for virus (lipid enveloped) inactivation purposes. Also other chemicals from the upstream Factor VIII purification can be present in the Factor VIII load solution, such as 0.2 mol/kg Sorbitol and 0.045 mol/kg arginine which can be added for Factor VIII stabilization purposes. Typically the Factor VIII load is about 5,000-about 25,000 IU/mL affinity resin and in principal any purity (1-15,000 IU Factor VIII/mg protein) of the Factor VIII solution could be applied to the affinity column. The process is performed at ambient temperature, e.g. room temperature.

After the Factor VIII containing solution has been processed over the column, the column is rinsed with 15 column volumes of equilibration buffer (0.3 mol/kg NaCl, 0.02 mol/kg $CaCl_2$, 0.02 mol/kg L-histidine, 0.02% (w/w) Polysorbate 80, pH 6.4-6.6, conductivity 30-36 mS/cm) to remove impurities (both product and process related). Followed by a 5 column volume wash with increased salt concentration (1 mol/kg NaCl, 0.02 mol/kg $CaCl_2$, 0.02 mol/kg L-histidine, 0.02% (w/w) Polysorbate 80, pH 6.4-6.6, conductivity 83-89 mS/cm) to specifically remove single FVIII light chain. Biologically active Factor VIII is thereafter eluted from the column using 4 column volumes of a buffer with increased salt concentration and etylenglycol (1.5 mol/kg NaCl, 0.02 mol/kg $CaCl_2$, 0.02 mol/kg L-histidine, 50% (w/w) ethylene glycol, 0.02% (w/w) Polysorbate 80, pH 6.4-6.6, conductivity 36-42 mS/cm).

Remaining proteins bound to the affinity resin is thereafter removed by an acidic wash (pH 2), where after the resin, after equilibration, is ready for another purification cycle.

Detailed Description of the Anion Exchange Chromatography Step

Factor VIII is bound to a strong anion exchange column (Q Sepharose FF) under equilibration buffer conditions (0.1 mol/kg NaCl, 0.02 mol/kg $CaCl_2$, 0.02 mol/kg L-histidine, 0.02% (w/w) Polysorbate 80, pH 7.4-7.6, conductivity 12-16 mS/cm). Also other chemicals from the upstream Factor VIII purification can be present in the Factor VIII load solution, such as 5% Etylene glycol. Typically the Factor VIII load is 10,000-100,000 IU/mL affinity resin and the purity of the starting material is >5000 IU Factor VIII/mg protein. The process is performed at ambient, e.g. room temperature.

After the Factor VIII containing solution has been processed over the column, the column is rinsed with 15 column volumes of equilibration buffer (0.1 mol/kg NaCl, 0.02 mol/kg $CaCl_2$, 0.02 mol/kg L-histidine, 0.02% (w/w) Polysorbate 80, pH 7.4-7.6, conductivity 12-16 mS/cm) to remove impurities (both product and process related). Followed by a 5 column volume wash with increased salt concentration (0.30 mol/kg NaCl, 0.02 mol/kg $CaCl_2$, 0.02 mol/kg L-histidine, 0.02% (w/w) Polysorbate 80, pH 7.4-7.6, conductivity 30-35 mS/cm) to remove inactive forms of Factor VIII. Biologically active monomeric Factor VIII is thereafter eluted from the column using one column volume of a buffer with increased salt concentration (0.39 mol/kg NaCl, 0.02 mol/kg $CaCl_2$, 0.02 mol/kg L-histidine, 0.02% (w/w) Polysorbate 80, pH 5.9-6.1, conductivity 38-42 mS/cm).

Any remaining proteins bound to the anion exchange resin by ionic interaction is thereafter removed by increasing the salt concentration to 2 mol/kg NaCl, whereafter the resin is sanitized using high pH (14) and after equilibration, the column is ready for another purification cycle.

Detailed Description of the Size Exclusion Chromatography Step

Factor VIII is loaded 4-8% of the column volume to a size exclusion chromatography column (Superdex 200 p.g.) with a bed height of 70 cm and equilibrated with; 30.7 g/kg NaCl, 0.5 g/kg $CaCl_2$, 2.0 g/kg Na-citrate, 9.2 g/kg L-arginine hydrochloride, 9.2 g/kg Sacharose 2.0 g/kg Poloxamer 188, pH 6.9-7.1, conductivity 47-51 mS/cm. Typically the Factor VIII concentration in the starting material is >10,000 IU/mL and the buffer composition; 0.4 mol/kg NaCl, 0.02 mol/kg $CaCl_2$, 0.02 mol/kg L-histidine, 0.02% (w/w) Polysorbate 80, pH 6.0-6.5, conductivity 35-42 mS/cm. The purity of the starting material is >8000 IU Factor VIII/mg protein. The process is performed in room temperature; 18-25° C.

After the Factor VIII containing solution has been applied on the size exclusion column, the column is processed with equilibration buffer until, at the outlet of the column, the absorbance as measured at 280 nm is raised to 40 mAU, when the monomer biologically active Factor VIII product is collected until the absorbance returns to its origin (40-1 mAU). Biological inactive aggregated Factor VIII are removed in front of (<40 mAU) and inactive Factor VIII fragment are removed after (<40 mAU), the monomeric biologically active Factor VIII peak. The monomeric biologically active Factor VIII solution after the size exclusion step, is typically 2-3 the volume of the starting material.

All references cited herein are incorporated by reference to the full extent to which the incorporation is not inconsistent with the expressed teachings herein. All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All headings and sub-headings are used herein for convenience only and should not be construed as limiting the invention in any way. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. This invention includes all modifications and equivalents of the subject matter recited in the claims and/or aspects included herein as permitted by applicable law.

The invention is further described but not limited by the following examples.

EXAMPLE 1

Purification with a yeast derived Factor VIII affinity ligand coupled on a resin.

The following process illustrates the removal of Factor VIII forms without Factor VIII:C activity on a yeast derived factor affinity ligand chromatography step (VIIISelect).

Column and Resin

A BPG140 column was packed with the VIIISelect resin to a bed height of eleven cm giving a column volume of 1.7 litres. The VIIISelect resin was obtained from GE Healthcare (Cat. No. 17-5450).

Starting Material:

A Factor VIII containing material with a purity of 1614 IU Factor VIII/mg protein, 0.34 mol/kg NaCl, 0.035 mol/kg CaCl$_2$, 0.01 mol/kg L-histidin, 0.045 mol/kg L-arginin, 0.2 mol/kg sorbitol, 0.02% (w/w) Polysorbat 80, 1% (w/w) Triton X-100, 0.3% tri-n-butyl phosphate (TNBP, w/w), pH 6.5 was used as starting material. The starting material was produced as further described in WO2009156430A1, incorporated by reference. The FVIII:C load on the resin was 15 529 IU/mL resin.

Buffer Compositions:

Equilibration buffer (with Triton X-100 and TNBP) 0.3 mol/kg NaCl, 0.02 mol/kg CaCl$_2$ (2×H$_2$O), 0.02 mol/kg L-histidine, 1% w/w Triton X-100, 0.3% w/w TNBP, pH: 6.5±0.1, conductivity: 31±3 mS/cm at +25° C.

Wash buffer 1 (Equilibration buffer without Triton X-100 and TNBP) 0.3 mol/kg NaCl, 0.02 mol/kg CaCl$_2$, 0.02 mol/kg L-histidine, 0.02% (w/w) Polysorbate 80, pH: 6.5±0.1, conductivity: 31±3 mS/cm at +25° C.

Wash Buffer 2

1.0 mol/kg NaCl, 0.02 mol/kg CaCl$_2$, 0.02 mol/kg L-histidine, 0.02% (w/w) Polysorbate 80, pH: 6.5±0.1, conductivity: 85±3 mS/cm at +25° C.

Elution Buffer 1.5 mol/kg NaCl, 0.02 mol/kg CaCl$_2$, 0.02 mol/kg L-histidine, 0.02% (w/w) Polysorbate 80, 50% (w/w) ethylene glycol (EG), pH: 6.5±0.1, conductivity: 39±3 mS/cm at +25° C.

The equilibration, washing and elution buffers are not limited to the stated pH, concentrations, and type of buffer, salts or detergent.

The column was equilibrated with equilibration buffer followed by loading of the starting material. The resin was thereafter subjected to wash buffer 1 and wash buffer 2 and thereafter the elution buffer as described in Table 1. Samples were taken from respectively fraction (flow through during load of starting material+wash 1, wash 2 and elution) and analyzed in regard of FVIII:C, FVIII:Ag and FVIII Western blot.

distinct major Factor VIII band which has the same molecular weight as the single (dissociated) Factor VIII light chain (80 kD). This Factor VIII fraction shows as well no or very little Factor VIII:C activity (as shown in Table 3). Lane 4 shows the elution fraction of the affinity step including the Factor VIII light chain (80 kD), the Factor VIII heavy chain (90 kD) and the uncleaved factor VIII molecule (170 kD).

CONCLUSION EXAMPLE 1

The VIIISelect step removes Factor VIII molecules with reduced and/or without FVIII:C activity in the flow through and wash fractions as can be seen in Table 3 and FIG. 1 (Lane 1-4).

EXAMPLE 2

Anion Exchange Chromatography Step (Q-Sepharose FF)

The following process illustrates the removal of Factor VIII forms without Factor VIII:C activity on an anion exchanger resin (Q Sepharose FF) resulting in a high Factor VIII monomer product.

Column and Resin

A BPG140 column was packed with the Q Sepharose FF resin to a bed height of eight cm giving a column volume of 1.23 litres. The Q Sepharose FF resin was obtained from GE Healthcare (Cat. 17-0510).

Starting Material

A Factor VIII containing material with a purity of 9470 IU Factor VIII/mg protein, 0.1 mol/kg NaCl, 0.02 mol/kg CaCl$_2$, 0.02 mol/kg L-histidin, 0.02% (w/w) Polysorbat 80, pH 6.5 was used as starting material. The starting material was produced as further described in example 1 (the product elution fraction). The FVIII:C load on the resin was 15,383 IU/mL resin.

TABLE 3

Results from VIIISelect processing

| Sample | Amount (kg) | FVIII:C (IU/ml)/ (MIU) | Total FVIII:C (%) | FVIII:Ag (IU/ml)/ (MIU) | Total FVIII:Ag (%) | Ratio (C/Ag) |
|---|---|---|---|---|---|---|
| Starting material (load) | 23.2 | 1140/26.4 | 100 | 1859/43.1 | 100 | 0.61 |
| Flow through + Wash 1 | 48.2 | 0.59/0.02 | 0.1 | 132/6.36 | 17 | <0.01 |
| Wash 2 | 16.9 | <0.5/<0.01 | 0.03 | 26.3/0.44 | 1.2 | <0.02 |
| Elution | 6.0 | 3572/21.4 | 81 | 4122/24.7 | 57 | 0.87 |

Table 3 illustrates the removal of inactive Factor VIII forms from the starting material. The ratio of biologically active Factor VIII as measured with FVIII:C in comparison with the total amount of available Factor VIII as measured through FVIII:Ag, was 0.61 in the starting material. The C/Ag ratio was also measured in the flow through and wash fractions, to be very low (<0.05). In the eluate fraction the C/Ag ratio has increased from 0.61 in the starting material, to 0.87. This clearly shows the removal of inactive Factor VIII forms over the VIIISelect affinity step. This is further confirmed when looking in FIG. 1 Factor VIII Western blot analysis, lane 1-4. Lane 1 shows the "starting material" before the affinity column. Lane 2 shows a lot of Factor VIII related bands which shows that Factor VIII degenerated products are removed in the "flow through+wash 1 fraction". Lane 3 shows that in the "wash 2 fraction" there is one Buffer Compositions:

Equilibration Buffer 0.1 mol/kg NaCl, 0.02 mol/kg CaCl$_2$ (2×H$_2$O), 0.02 mol/kg L-histidine, 0.02% (w/w) Polysorbate 80, pH: 7.5±0.1, conductivity: 15±1 mS/cm at +25° C.

Wash Buffer 0.32 mol/kg NaCl, 0.02 mol/kg CaCl$_2$, 0.02 mol/kg L-histidine, 0.02% (w/w) Polysorbate 80, pH: 7.5±0.1, conductivity: 32.5±2.5 mS/cm at +25° C.

Elution Buffer 0.39 mol/kg NaCl, 0.02 mol/kg CaCl$_2$, 0.02 mol/kg L-histidine, 0.02% (w/w) Polysorbate 80, pH: 6.0±0.1, conductivity: 40±2 mS/cm at +25° C.

The equilibration, washing and elution buffers are not limited to the stated pH, concentrations, and type of buffer, salts or detergent.

The column was equilibrated with equilibration buffer followed by loading of the starting material. The resin was thereafter subjected to equilibration buffer again to allow Factor VIII to bind and thereafter the wash buffer was applied followed by the elution buffer, as described in Table 3. Samples were taken from respectively fraction (flow through during load of starting material+wash 1, wash 2 and elution) and analyzed in regard of FVIII:C, FVIII:Ag, SEC-HPLC1,FVIII Western blot, N-Glycan fingerprint mapping and trypsin peptide fingerprint mapping.

TABLE 4

Results from the anion exchange process

| Sample | Amount (kg) | FVIII:C (IU/ml)/ (MIU) | Total FVIII:C (%) | FVIII:Ag (IU/ml)/ (MIU) | Total FVIII:Ag (%) | Ratio (C/Ag) |
|---|---|---|---|---|---|---|
| Starting material (load) | 58.4 | 324/18.9 | 100 | 412/24.1 | 100 | 0.78 |
| Flow through + Equil. | 71.8 | 1.7/0.11 | 0.6 | 15.4/1.1 | 4.6 | 0.11 |
| Wash | 6.2 | 130/0.81 | 4.3 | 401/2.5 | 10 | 0.32 |
| Elution | 0.958 | 16410/15.7 | 83 | 18131/17.4 | 72 | 0.91 |

Figure 2:
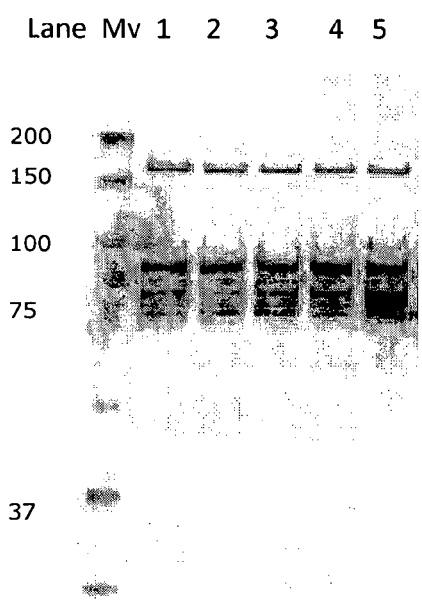
FIG. 2: Western blot using FVIII antibodies. From left molecular weight standard, Lane 1; FVIII control, FVIII:C 5.0 IU/mL, Lane 2; Affinity eluate, FVIII:C 5 IU/ml, Lane 3; diluted affinity eluate, FVIII:C 5 IU/ml, Lane 4; anion exchange eluate, FVIII:C 5 IU/ml, Lane 5; Size exclusion eluate, FVIII:C 5 IU/ml.
Figure 4:
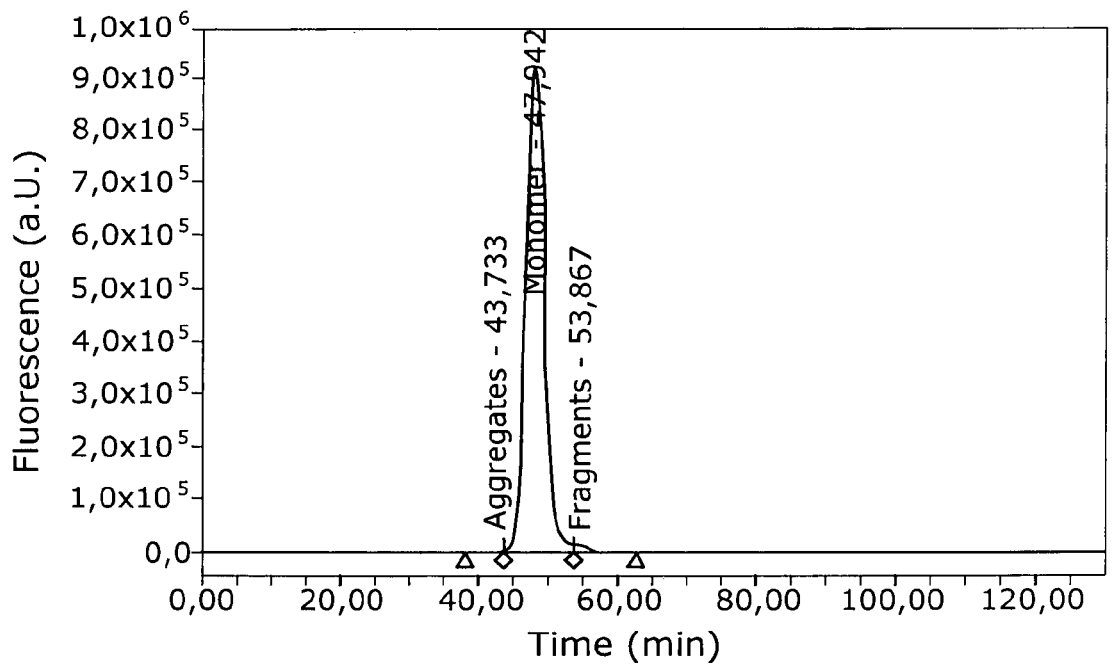
FIG. 4: A chromatogram from an analytical size exclusion chromatography column (SEC-HPLC1) showing the chromatographic profile from a sample (elution) prepared according to example 2 and it's respectively aggregate, monomer and fragment content in percentage. The monomer content of this sample is >98% with <0.5% of aggregate and <1.5% fragments.

Table 4 illustrates the removal of inactive Factor VIII forms from the starting material of the anion exchange step. The ratio of biologically active Factor VIII as measured with FVIII:C in comparison with the total amount of available Factor VIII as measured through FVIII:Ag, was 0.78 in the starting material. The C/Ag ratio was also measured in the flow through and wash fractions, to be significantly lower (<0.35). In the eluate fraction the C/Ag ratio has increased from 0.78 in the starting material, to 0.91. This clearly shows the removal of inactive Factor VIII forms over the anion exchange step. This is further confirmed when looking in FIG. 1, lane 5-6, in which both shows Factor VIII degenerated products are removed in the flow through+equilibration fraction and in the wash fraction. FIG. 2, lane 4, shows the FVIII Western blot profile of the Factor VIII main fraction (eluate), without visible FVIII degeneration products. The high (>98%) monomeric content, as analysed with SEC-HPLC1, in the eluate is shown in FIG. 4.

CONCLUSION EXAMPLE 2

The anion exchange step removes Factor VIII molecules with reduced and/or without FVIII:C activity in the flow through and wash fractions as can be seen in Table 4 and FIG. 1 (Lane 5-6). The biologically active product fraction (elution) contains highly monomeric Factor VIII, as can be seen in FIG. 4.

EXAMPLE 3

Size Exclusion Chromatography

The following process illustrates the removal of Factor VIII forms without Factor VIII:C activity on a size exclusion chromatography column (Superdex 200 p.g.).
Column and Resin
A BPG100 column was packed with Superdex 200 p.g. resin to a bed height of 69 cm giving a column volume of 5.4 litres. The Superdex 200 p.g. resin was obtained from GE Healthcare (Cat. No. 17-1043).

Starting Material
A Factor VIII containing material with a purity of 10 200 IU Factor VIII/mg protein, 0.4 mol/kg NaCl, 0.02 mol/kg CaCl$_2$, 0.02 mol/kg L-histidin, 0.02% (w/w) Polysorbat 80, pH 6.2 was used as starting material. The starting material was produced as described in example 2 (the product elution fraction). The sample load on the resin was 5.5% of the column volume.

Buffer Composition:
Equilibration Buffer
30.7 g/kg NaCl, 0.5 g/kg CaCl$_2$, 2.0 g/kg sodium citrate, 9.2 g/kg arginine, 9.2 g/kg sucrose, 0.02% (w/w) Polysorbate 80, pH: 7.0±0.1, conductivity: 49±2 mS/cm at +25° C.

The equilibration is not limited to the stated pH, concentrations, and type of buffer, salts or detergent.

The column was equilibrated with equilibration buffer followed by loading of the starting material. The resin was thereafter subjected to equilibration buffer again to allow the Factor VIII solution to separate over the size exclusion column. When the absorbance at 280 nm was raised over 0.035 AU at the outlet of the column, the collection of the eluate was started and when the absorbance was decreased to 0.05, the collection of the eluate was stopped. Samples were taken from the load and the eluate and analyzed in regard of FVIII:C, FVIII:Ag, SEC-HPLC1 and FVIII Western blot.

TABLE 5

Results from the size exclsuion process

| Sample | Amount (mL) | FVIII:C (IU/ml)/ (MIU) | Total FVIII:C (%) | FVIII:Ag (IU/ml)/ (MIU) | Total FVIII:Ag (%) | Ratio (C/Ag) |
|---|---|---|---|---|---|---|
| Starting material (load) | 489 | 14633/7.2 | 100 | 17582/8.6 | 100 | 0.83 |
| Elution | 1190 | 6399/7.6 | 106% | 6780/8.1 | 94 | 0.94 |

Figure 3:
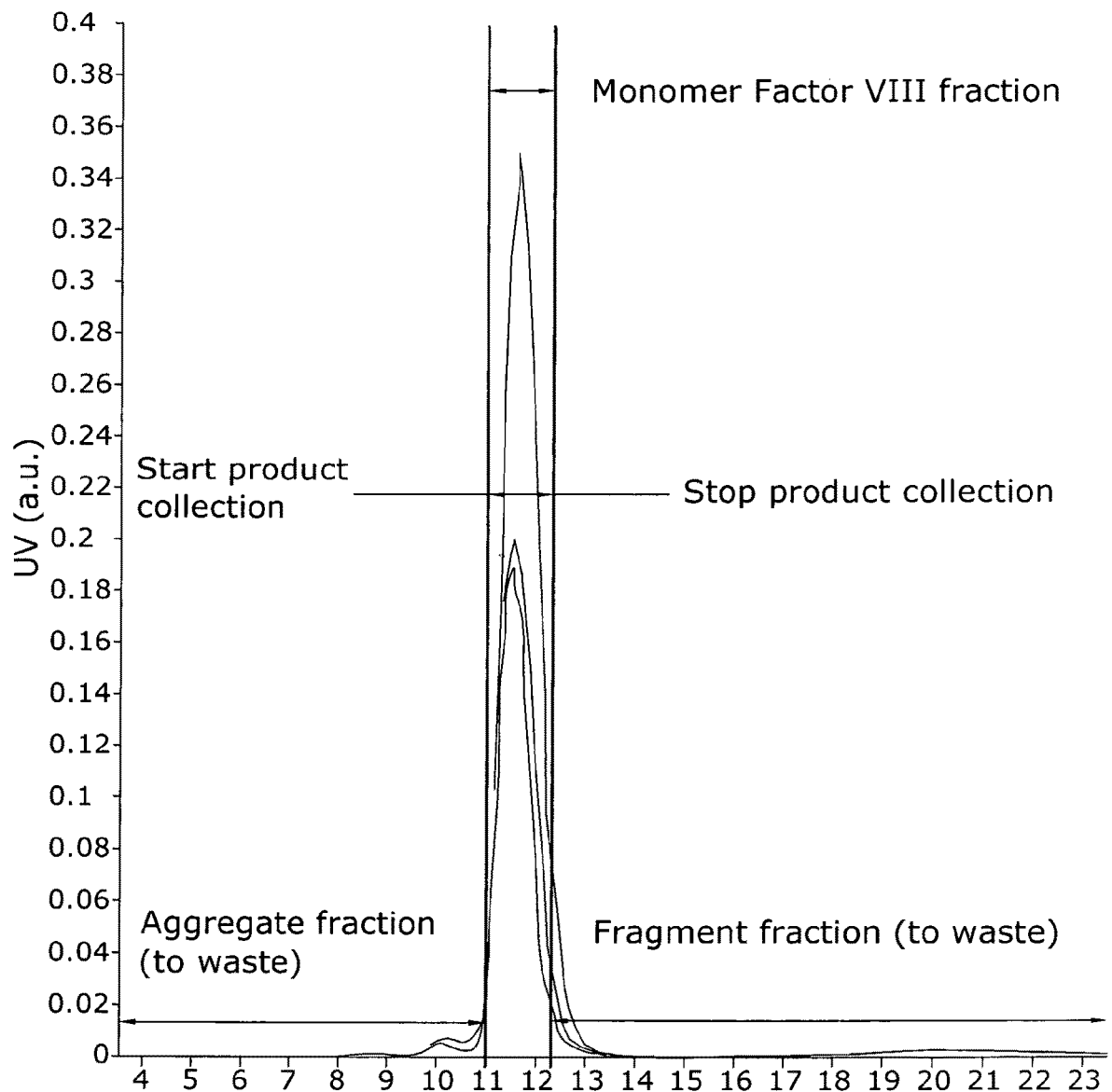
FIG. 3: A chromatogram from a preparative size exclusion chromatography column according to example 3, showing separation of aggregates and fragment from monomer Factor VIII for 3 different experiments using different resin load and Factor VIII concentration. The equilibration buffer system and chromatography conditions according to example 3, facilitates the aggregation and thus the removal of aggregates from monomermonomer Factor VIII (elution). The chromatography peaks reflects proteins measured at an absorbance at 280 nm.
Figure 5:
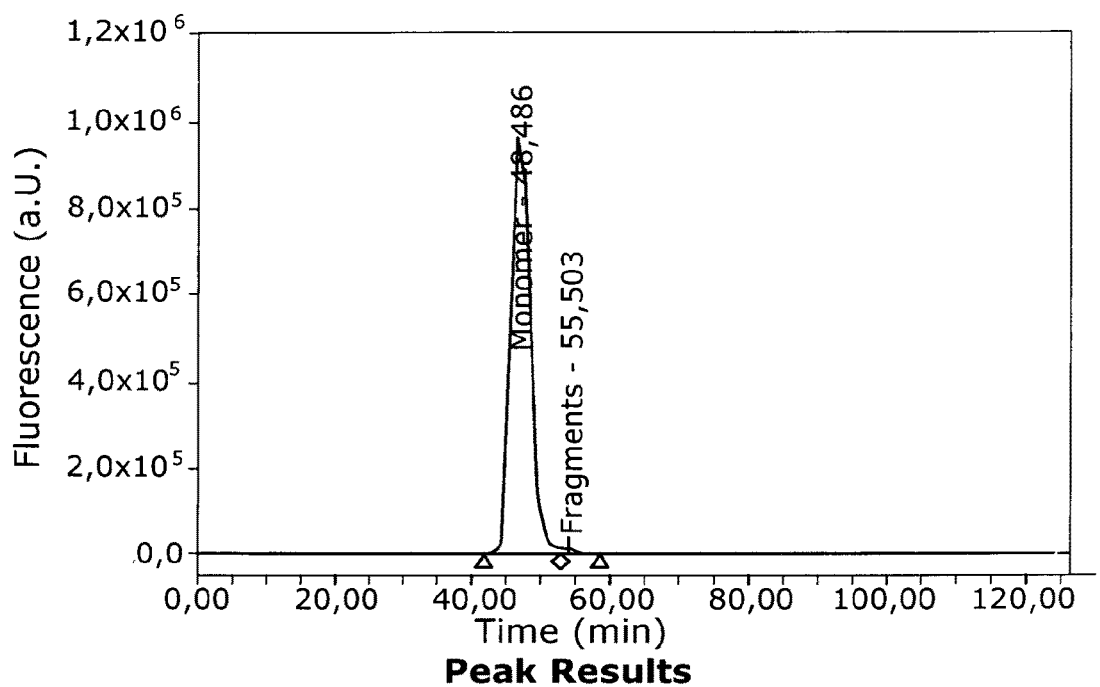
FIG. 5: A chromatogram from an analytical size exclusion chromatography column (SEC-HPLC1) showing the chromatographic profile from a sample (elution) prepared according to example 3 and it's respectively aggregate, monomer and fragment content in percentage. The monomer content of this sample is typically >99% with no visible amount of aggregates and <1% of fragments.

Table 5 illustrates the removal of inactive Factor VIII forms from the starting material over the size exclusion step. The ratio of biologically active Factor VIII as measured with FVIII:C in comparison with the total amount of available Factor VIII as measured through FVIII:Ag, was 0.83 in the starting material and 0.94 in the eluate fraction. This indicates the removal of inactive Factor VIII forms over the size exclusion column due to either aggregation and/or fragmentation. FIG. 2, lane 5 show equal Factor VIII band pattern profile for the elution fraction compared to control. FIG. 5, shows the high (>99%) Factor VIII monomer and low (<1%)

aggregate content of the eluate using the SEC-HPLC1 analysis under native conditions. FIG. 3 illustrates the actual removal of aggregate and fragment from a monomer Factor VIII product, as depictured from a production size exclusion chromatogram.

CONCLUSION EXAMPLE 3

The size exclusion chromatography step removes Factor VIII molecules with reduced and/or without FVIII:C activity through separation of molecules of different size. The chromatography environment and process parameters facilitates the aggregation and removal of these during the procedure, resulting in a highly (>99%) monomer Factor VIII product with a high biological activity (C/Ag >0.9), as can be seen in FIG. 5 and Table 5.

EXAMPLE 4

Sequential Use of Affinity-, Anion Exchange- and Size Exclusion Chromatography

The following process illustrates the removal of Factor VIII forms without Factor VIII:C activity performing a purification sequence consisting of three different chromatography techniques processed in sequence:
1. Affinity chromatography (VIIISelect)
2. Anion Exchange Chromatography (Q Sepharose FF)
3. Size exclusion chromatography (Superdex 200 p.g.)
Columns and Resins
1. Affinity Chromatography (VIIISelect)
A BPG140 column was packed with the VIIISelect resin to a bed height of ten cm giving a column volume of 1.5 litres. The VIIISelect resin was obtained from GE Healthcare (Cat. No. 17-5450).
2. Anion Exchange Chromatography (Q Sepharose FF)
A BPG100 column was packed with the Q Sepharose FF resin to a bed height of seven cm giving a column volume of 0.55 litres. The Q Sepharose FF resin was obtained from GE Healthcare (Cat. 17-0510).
3. Size Exclusion Chromatography (Superdex 200 p.g.)
A BPG100 column was packed with Superdex 200 p.g. resin to a bed height of 69 cm giving a column volume of 5.4 litres. The Superdex 200 p.g. resin was obtained from GE Healthcare (Cat. No. 17-1043).
Starting Material, Buffer Composition Affinity Step:
0.34 mol/kg NaCl, 0.035 mol/kg $CaCl_2$, 0.01 mol/kg L-histidin, 0.045 mol/kg L-arginin, 0.2 mol/kg sorbitol, 0.02% (w/w) Polysorbat 80, 1% (w/w) Triton X-100, 0.3% tri-n-butyl phosphate (TNBP, w/w), pH 6.5 was used as starting material. The starting material was produced as further described in WO 2009/156430 A1, incorporated by reference.
Starting Material, Buffer Composition Anion Exchange Step:
0.15 mol/kg NaCl, 0.02 mol/kg $CaCl_2$, 0.02 mol/kg L-histidin, 0.02% (w/w) Polysorbat 80, pH 7.5 was used as starting material.
Starting Material Buffer Composition Size Exclusion Step:
0.39 mol/kg NaCl, 0.02 mol/kg $CaCl_2$, 0.02 mol/kg L-histidin, 0.02% (w/w) Polysorbat 80, pH 6.2 was used as starting material.
Buffer Compositions Affinity Chromatography:
Equilibration Buffer (with Triton X-100 and TNBP)
0.3 mol/kg NaCl, 0.02 mol/kg $CaCl_2$ ($2×H_2O$), 0.02 mol/kg L-histidine, 1% w/w Triton X-100, 0.3% w/w TNBP, pH: 6.5±0.1, conductivity: 31±3 mS/cm at +25° C.

Wash Buffer 1 (Equilibration Buffer without Triton X-100 and TNBP)
0.3 mol/kg NaCl, 0.02 mol/kg $CaCl_2$, 0.02 mol/kg L-histidine, 0.02% (w/w) Polysorbate 80, pH: 6.5±0.1, conductivity: 31±3 mS/cm at +25° C.
Wash Buffer 2
1.0 mol/kg NaCl, 0.02 mol/kg $CaCl_2$, 0.02 mol/kg L-histidine, 0.02% (w/w) Polysorbate 80, pH: 6.5±0.1, conductivity: 85±3 mS/cm at +25° C.
Elution Buffer
1.5 mol/kg NaCl, 0.02 mol/kg $CaCl_2$, 0.02 mol/kg L-histidine, 0.02% (w/w) Polysorbate 80, 50% (w/w) ethylene glycol (EG), pH: 6.5±0.1, conductivity: 39±3 mS/cm at +25° C.
The equilibration, washing and elution buffers are not limited to the stated pH, concentrations, and type of buffer, salts or detergent.
Buffer Compositions Anion Exchange Chromatography:
Equilibration Buffer
0.1 mol/kg NaCl, 0.02 mol/kg $CaCl_2$ ($2×H_2O$), 0.02 mol/kg L-histidine, 0.02% (w/w) Polysorbate 80, pH: 7.5±0.1, conductivity: 15±1 mS/cm at +25° C.
Wash Buffer
0.32 mol/kg NaCl, 0.02 mol/kg $CaCl_2$, 0.02 mol/kg L-histidine, 0.02% (w/w) Polysorbate 80, pH: 7.5±0.1, conductivity: 32.5±2.5 mS/cm at +25° C.
Elution Buffer 0.39 mol/kg NaCl, 0.02 mol/kg $CaCl_2$, 0.02 mol/kg L-histidine, 0.02% (w/w) Polysorbate 80, pH: 6.0±0.1, conductivity: 40±2 mS/cm at +25° C.
The equilibration, washing and elution buffers are not limited to the stated pH, concentrations, and type of buffer, salts or detergent.
Buffer Compositions Size Exclusion Chromatography:
Equilibration Buffer
30.7 g/kg NaCl, 0.5 g/kg $CaCl_2$, 2.0 g/kg sodium citrate, 9.2 g/kg arginine, 9.2 g/kg sucrose, 0.02% (w/w) Polysorbate 80, pH: 7.0±0.1, conductivity: 49±2 mS/cm at +25° C.
The equilibration is not limited to the stated pH, concentrations, and type of buffer, salts or detergent.
The respective column (affinity-, anion exchange-, size exclusion chromatography) was equilibrated with equilibration buffer as defined above.
The affinity chromatography resin was processed first, by loading the starting material as defined above and in Table 6, followed by washing the column with wash buffer 1 and wash buffer 2, as defined above. Thereafter the biologically active Factor VIII product was eluted through the elution buffer. The eluate was, after sampling (FVIII:C, FVIII:Ag) the starting material for the following anion exchange chromatography step.
The eluate from the affinity chromatography step was diluted 10 times to achieve the starting material conditions as defined above. The diluted start material was processed over the anion exchange column followed by wash 1 and wash 2, as defined above. Thereafter the biologically active Factor VIII product was eluted through the elution buffer. The eluate was, after sampling (FVIII:C, FVIII:Ag), the starting material for the following size exclusion chromatography step.
The eluate from the anion exchange step was thawed if frozen, otherwise processed directly over the size exclusion chromatography step, as defined above and in Table 6. After product application onto the column, equilibration buffer was processed over the column until the monomer Factor VIII fraction was eluted. The monomer Factor VIII fraction was started when the absorbance, as measured at 280 nm, rose above 0.04 AU. And the monomer Factor VIII fraction collection was stopped when the absorbance, as measured at 280 nm, went back to 0.01 AU. The eluate was sampled and analyzed for; FVIII:C, FVIII:Ag, FVIII Western blot, SEC_HPLC and amino acid composition.

The above described procedure was repeated for 5 different batches under specified conditions (Table 6) to study reproducibility, which result can be seen in Table 7.

TABLE 6

Column loading properties of 5 different batches

| Batch | Affinity | | Anion exchange | | Size exclusion | |
|---|---|---|---|---|---|---|
| | FVIII:C IU/mL | FVIII:C IU/mL resin | FVIII:C IU/mL | IU/mL resin | FVIII:C IU/mL | Column load (%) |
| Batch 1 | 993 | 7987 | 281 | 13016 | 12187 | 8 |
| Batch 2 | 1165 | 9003 | 315 | 14671 | 14601 | 5/4* |
| Batch 3 | 652 | 9355 | 360 | 14735 | 14559 | 5/5* |
| Batch 4 | 775 | 11114 | 342 | 17631 | 15067 | 5/5* |
| Batch 5 | 628 | 8423 | 317 | 14405 | 16058 | 7 |

*The size exclusion column was performed in 2 cycles, to not exceed the specified max column load of 8%, where after the two received eluates were mixed into one pool, from which the analytical samples was withdrawn.

TABLE 7

FVIII C/Ag results from the sequential purification process

| Batch | Start VIIISelect | | | VIIISelect eluate | | | Anion exchange eluate | | | Size exclusion eluate | | |
|---|---|---|---|---|---|---|---|---|---|---|---|---|
| | FVIII:C (IU/mL) | FVIII:Ag (IU/mL) | Ratio C/Ag | FVIII:C (IU/mL) | FVIII:Ag (IU/mL) | Ratio C/Ag | FVIII:C (IU/mL) | FVIII:Ag (IU/mL) | Ratio C/Ag | FVIII:C (IU/mL) | FVIII:Ag (IU/mL) | Ratio C/Ag |
| 1 | 1005 | 1455 | 0.69 | 3087 | 3841 | 0.80 | 13016 | 15617 | 0.83 | 6923 | 7242 | 0.96 |
| 2 | 632 | 924 | 0.68 | 3170 | 4202 | 0.75 | 14671 | 17533 | 0.84 | 5202 | 5450 | 0.95 |
| 3 | 755 | 1027 | 0.74 | 3442 | 4513 | 0.76 | 14735 | 16276 | 0.91 | 5602 | 5939 | 0.94 |
| 4 | 966 | 1433 | 0.67 | 3887 | 4424 | 0.88 | 17631 | 20076 | 0.88 | 7126 | 6519 | 1.09 |
| 5 | 755 | 1020 | 0.74 | 2796 | 3547 | 0.79 | 14405 | 18406 | 0.78 | 7144 | 8848 | 0.81 |
| Mean | 823 | 1172 | 0.70 | 3276 | 4105 | 0.80 | 14892 | 17582 | 0.85 | 6399 | 6800 | 0.95 |
| SD | | | 0.03 | | | 0.05 | | | 0.05 | | | 0.10 |

Table 7 illustrates the removal of inactive Factor VIII forms from the starting material, from five different batches, over the first purification step of the process (affinity chromatography), followed by the second purification step of the process (anion exchange chromatography) and finally the last purification step of the process (size exclusion chromatography).

Figure 6:
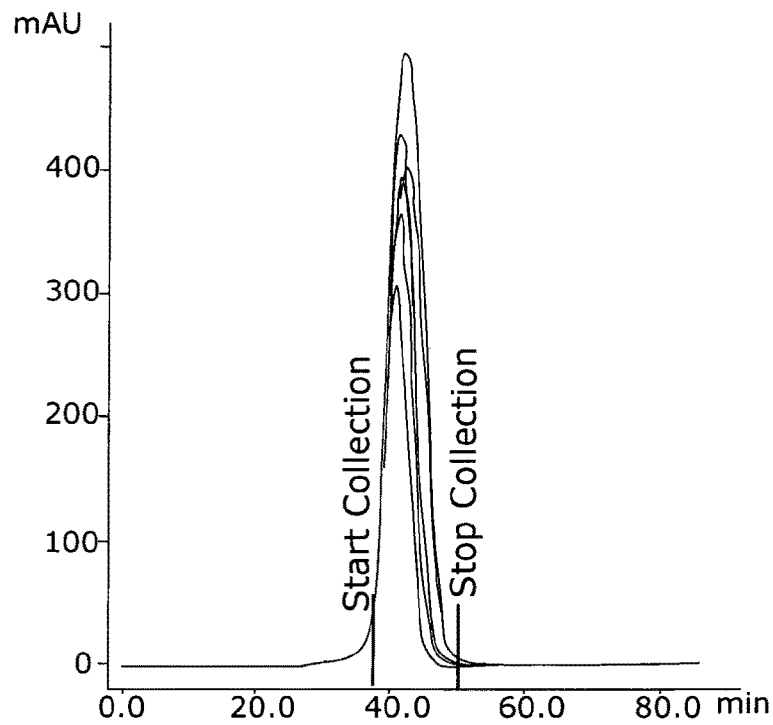
FIG. 6: A chromatogram from a preparative size exclusion chromatography column according to example 4, showing separation of aggregates and fragment from monomer Factor VIII for 5 different experiments using different resin load and Factor VIII concentration. The equilibration buffer system and chromatography conditions according to example 4, facilitates the aggregation and thus the removal of aggregates from monomer Factor VIII (elution). The chromatography peaks reflects proteins measured at an absorbance at 280 nm.
Figure 7:
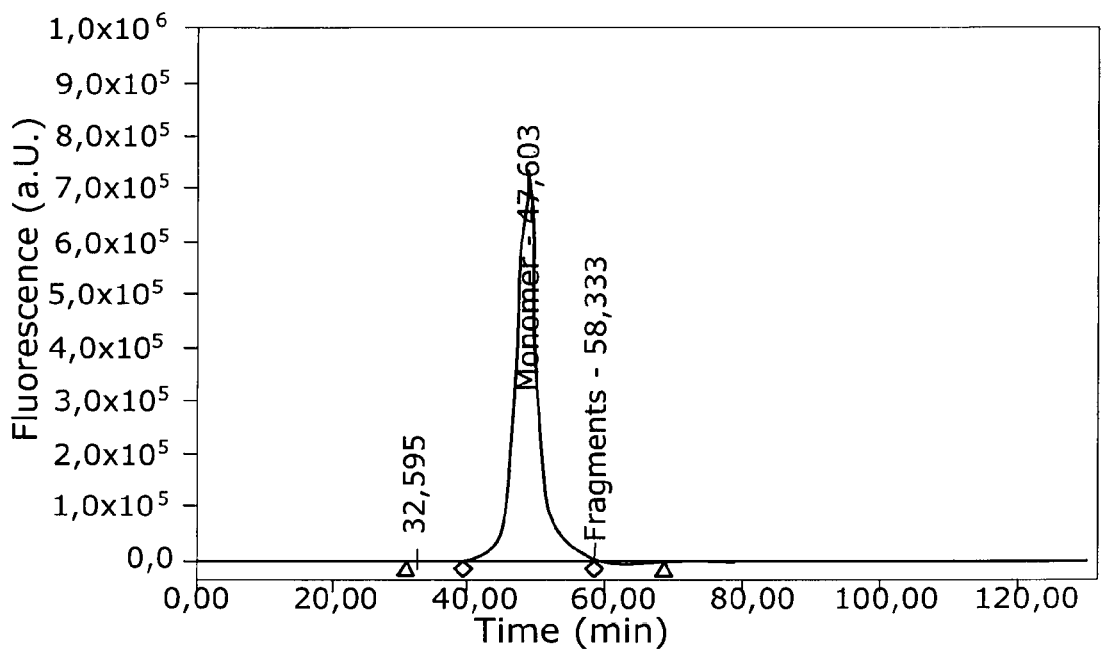
FIG. 7: A chromatogram from an analytical size exclusion chromatography column (SEC-HPLC1) showing the chromatographic profile from a sample prepared according to example 4 (anion exchange eluate) and it's respectively aggregate, monomer and fragment content in percentage. The monomer content of this sample is >97% with <0.7% of aggregates and fragments <2.5%.
Figure 8:
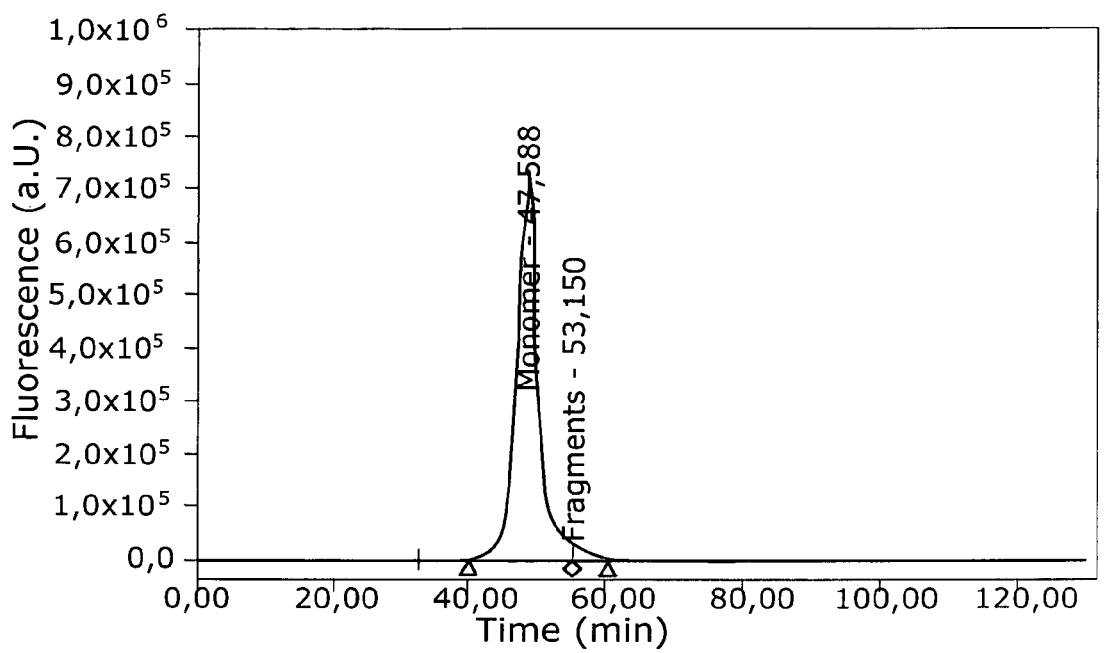
FIG. 8: A chromatogram from an analytical size exclusion chromatography column (SEC-HPLC1) showing the chromatographic profile from a sample prepared according to example 4 (size exclusion eluate) and it's respectively aggregate, monomer and fragment content in percentage. The monomer content of this sample is >98% with no visible signs of aggregates and fragments <2%.
Figure 9:
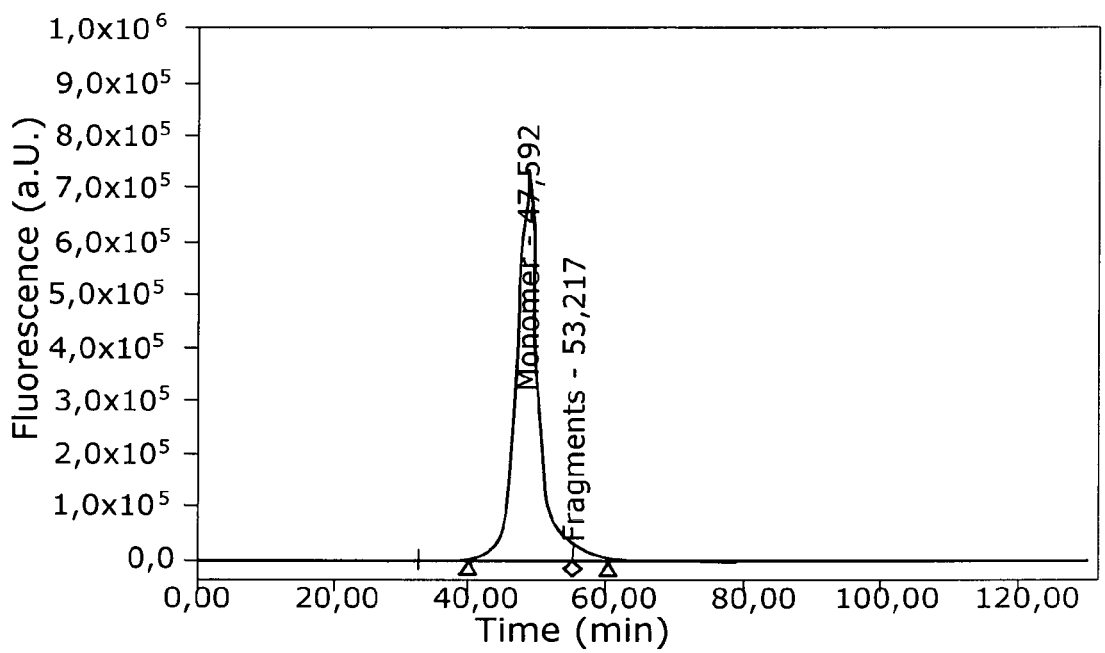
FIG. 9: A chromatogram from an analytical size exclusion chromatography column (SEC-HPLC1) showing the chromatographic profile from a sample prepared according to example 4 (anion exchange eluate) and it's respectively aggregate, monomer and fragment content in percentage. The monomer content of this sample is >98% with no visible signs of aggregates and fragments <2%.
Figure 10:
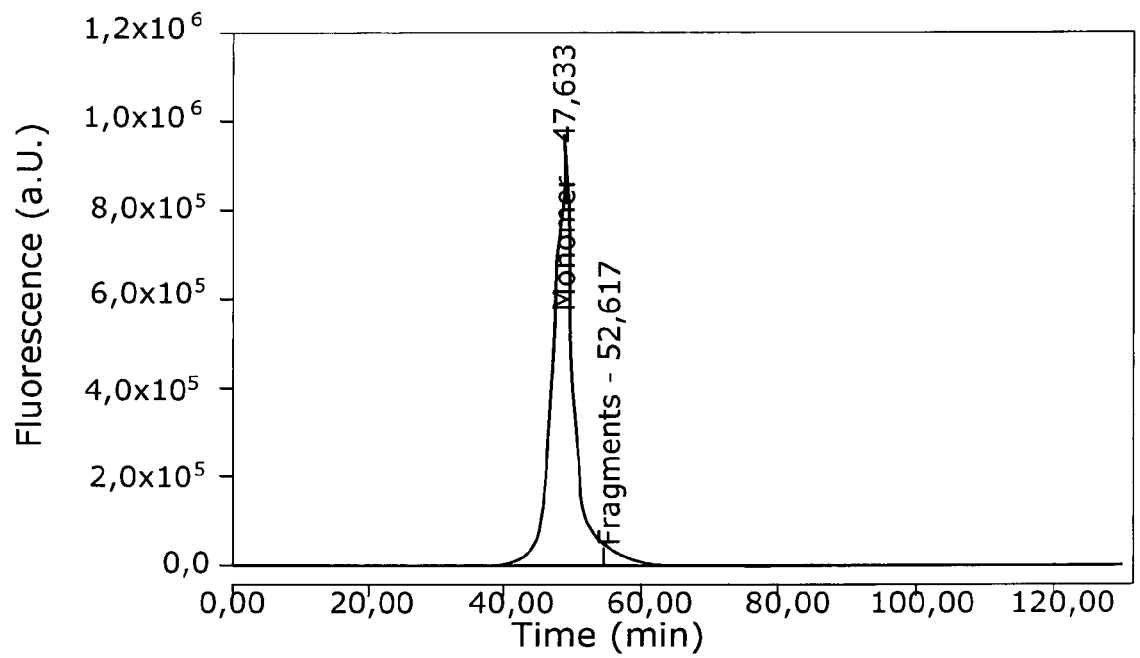
FIG. 10: A chromatogram from an analytical size exclusion chromatography column (SEC-HPLC1) showing the chromatographic profile from a sample prepared according to example 4 (size exclusion eluate) and it's respectively aggregate, monomer and fragment content in percentage. The monomer content of this sample is >98% with no visible signs of aggregates and fragments <2%.
Figure 11:
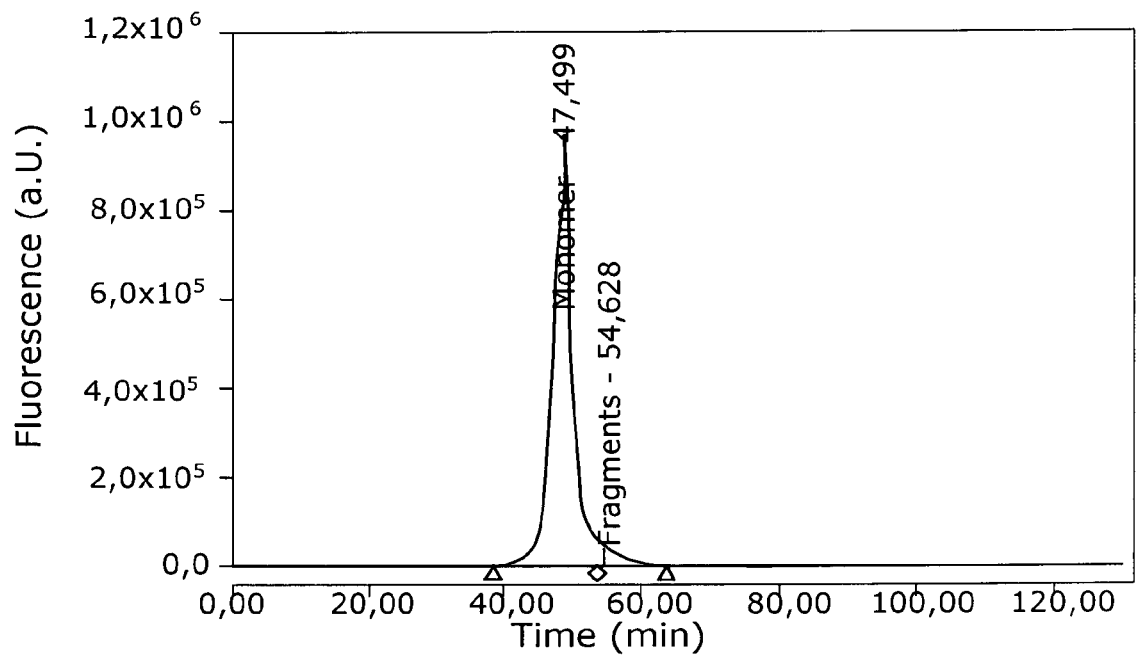
FIG. 11: A chromatogram from an analytical size exclusion chromatography column (SEC-HPLC1) showing the chromatographic profile from a sample prepared according to example 4 (anion exchange elution) and it's respectively aggregate, monomer and fragment content in percentage. The monomer content of this sample is >98% with no visible signs of aggregates and fragments <1.5%.
Figure 12:
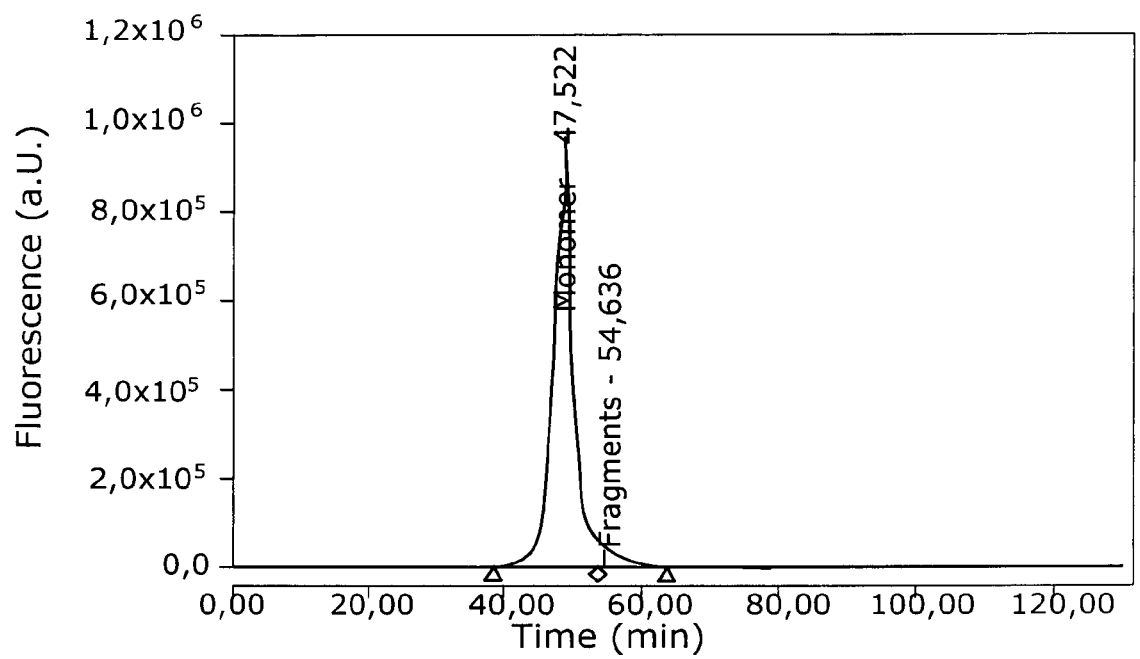
FIG. 12: A chromatogram from an analytical size exclusion chromatography column (SEC-HPLC1) showing the chromatographic profile from a sample prepared according to example 4 (size exclusion eluate) and it's respectively aggregate, monomer and fragment content in percentage. The monomer content of this sample is >98% with no visible signs of aggregates and fragments <1.5%.
Figure 13:
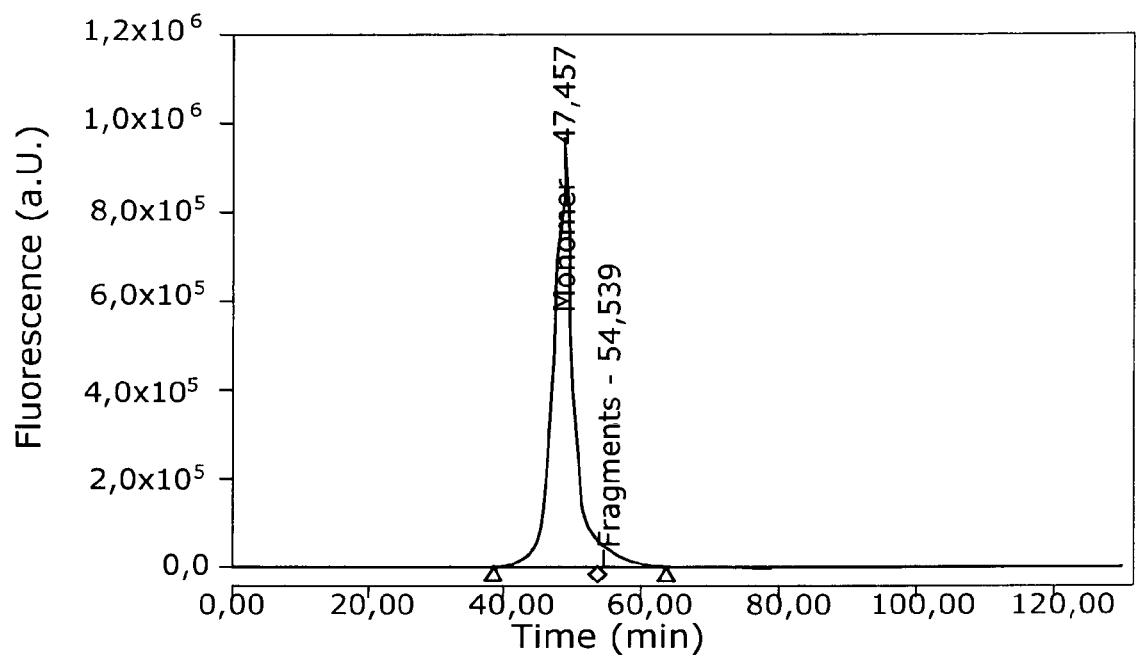
FIG. 13: A chromatogram from an analytical size exclusion chromatography column (SEC-HPLC1) showing the chromatographic profile from a sample prepared according to example 4 (anion exchange eluate) and it's respectively aggregate, monomer and fragment content in percentage. The monomer content of this sample is >99% with no visible signs of aggregates and fragments <1.5%.
Figure 14:
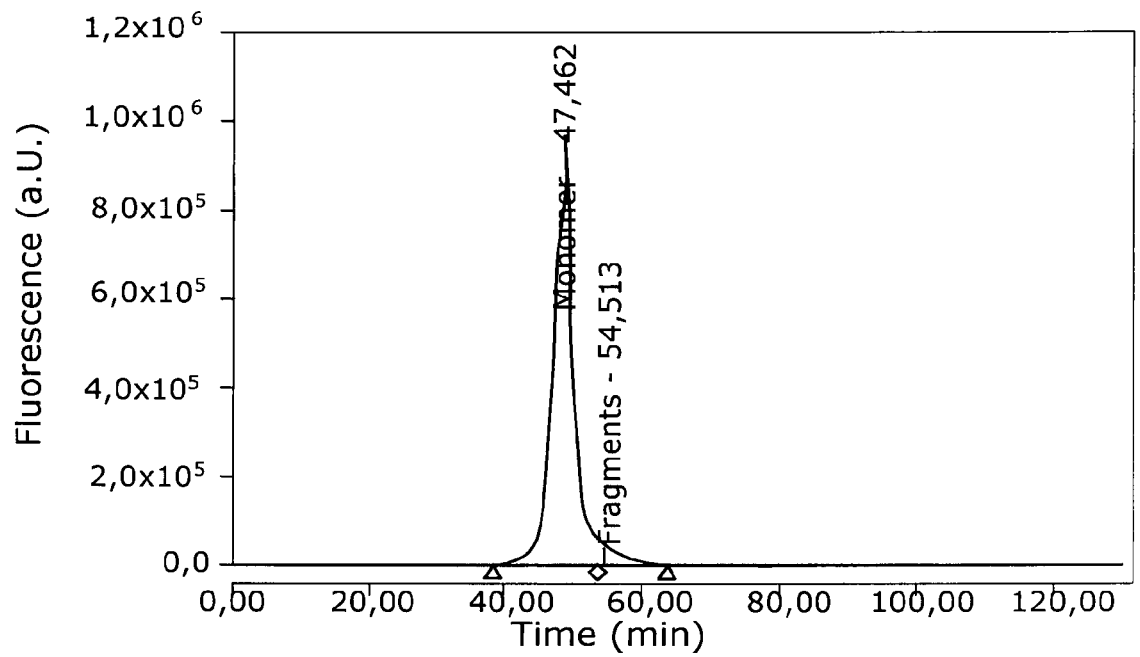
FIG. 14: A chromatogram from an analytical size exclusion chromatography column (SEC-HPLC1) showing the chromatographic profile from a sample prepared according to example 4 (size exclusion eluate) and it's respectively aggregate, monomer and fragment content in percentage. The monomer content of this sample is >98% with no visible signs of aggregates and fragments <1.5%.
Figure 15:
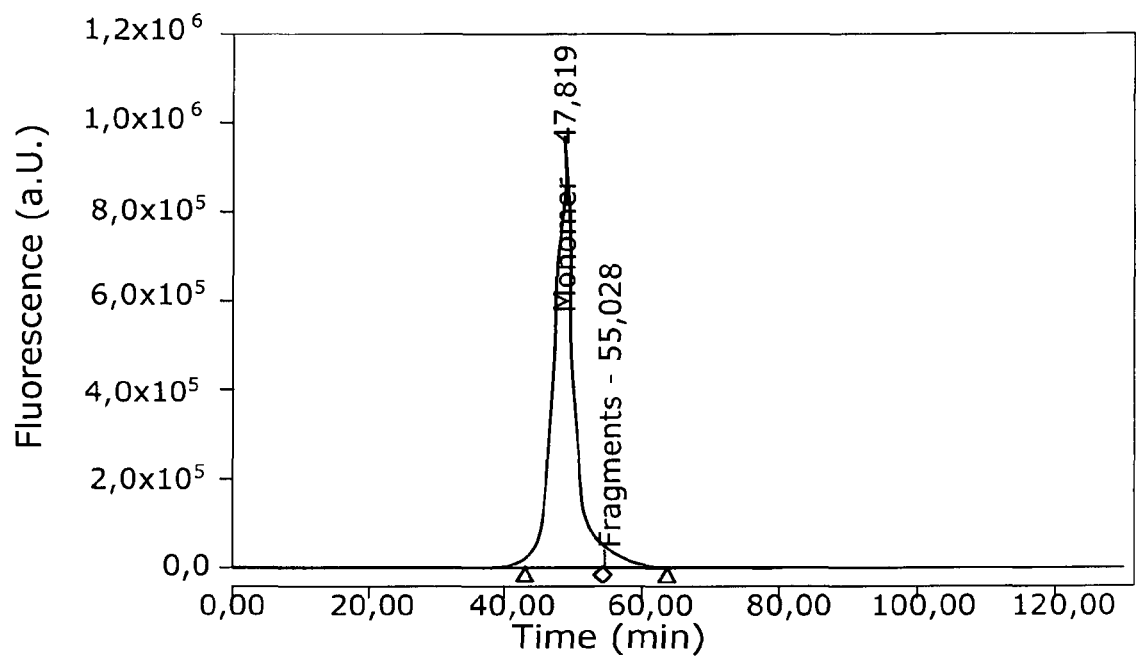
FIG. 15: A chromatogram from an analytical size exclusion chromatography column (SEC-HPLC1) showing the chromatographic profile from a sample prepared according to example 4 (anion exchange eluate) and it's respectively aggregate, monomer and fragment content in percentage. The monomer content of this sample is >99% with no visible signs of aggregates and fragments <1%.
Figure 16:
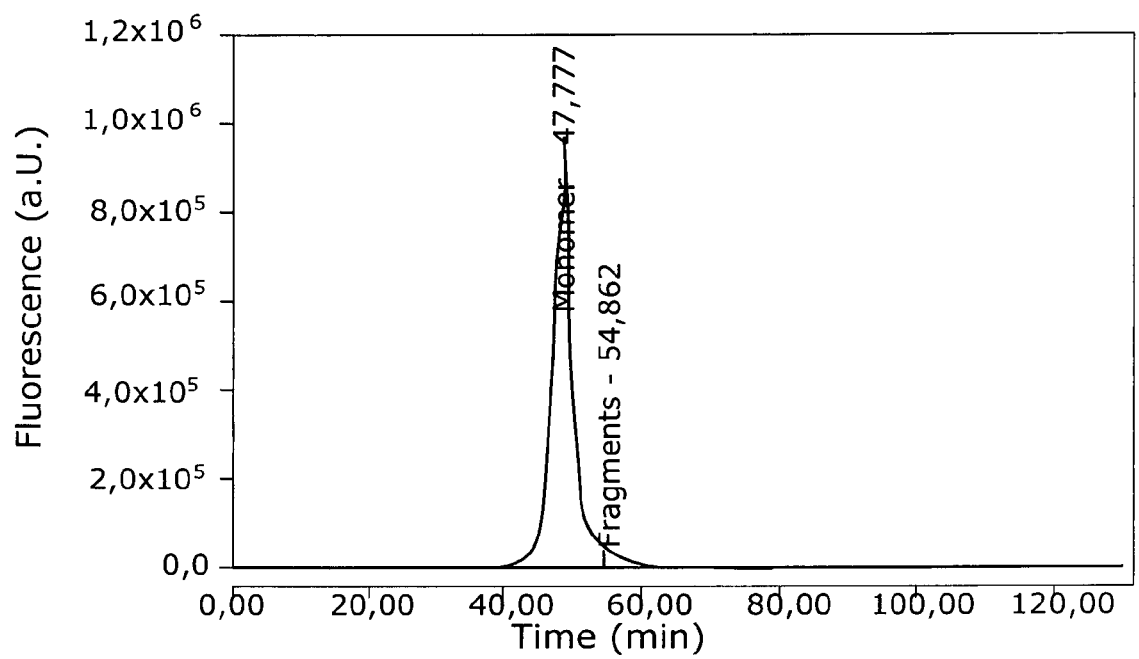
FIG. 16: A chromatogram from an analytical size exclusion chromatography column (SEC-HPLC1) showing the chromatographic profile from a sample prepared according to example 4 (size exclusion eluate) and it's respectively aggregate, monomer and fragment content in percentage. The monomer content of this sample is >98% with no visible signs of aggregates and fragments <1.5%.
Figure 17:
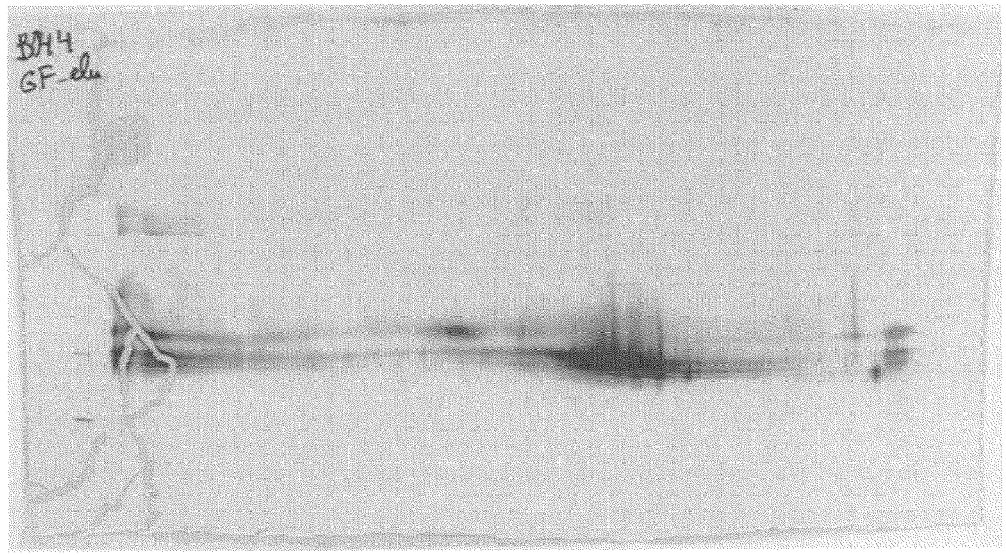
FIG. 17: Analytical two dimension electrophoresis (2D-PAGE) fingerprint of charge and size profile of a sample processed according to the invention example 4 sample after size exclusion chromatography.

FIG. 6 shows a chromatography overlay of the 5 production batches (according to Table 6-7) performed on the size exclusion chromatography step. The start and the stop of the collected size exclusion eluate fraction is indicated in the figure.

The ratio of biologically active Factor VIII as measured with FVIII:C in comparison with the total amount of available Factor VIII as measured through FVIII:Ag, was 0.70 as a mean value for the starting material before the affinity step. The FVIII C/Ag ratio increases then to 0.80 as a mean value after the affinity step and further increases to 0.85 as an average value after the anion exchange step. And finally ends up at 0.95 after the final size exclusion purification step, close to the optimal FVIII C/Ag ratio 1.0. This can further be studied in Table 7, showing all the FVIII:C and FVIII:Ag concentrations and the ratio FVIII:C/FVIII:Ag for respectively step for all 5 batches performed.

FIGS. 7, 9, 11, 13 and 15 show the results after SEC-HPLC1 analysis of the anion exchange eluate for batch 1-5 as defined in Table 6-7. The SEC-HPLC1 results for all anion exchange eluate samples shows no (4 batches) or very low (<1%) amount of aggregates (mean value for the 5 batches of 0.1%), a FVIII monomer content of >97% (mean value for the 5 batches of 98.5%) and fragment content of <2% (mean value for the 5 batches of 1.4%). The anion exchange eluate after performing the affinity step followed by the anion exchange step, shows a high content of Factor VIII monomer and a low content of potential immunogenic aggregate/fragment FVIII parts.

FIGS. 8, 10, 12, 14 and 16 show the results after SEC-HPLC1 analysis of the size exclusion eluate for batch 1-5 as defined in Table 6-7. The SEC-HPLC1 results for all size exclusion eluate samples shows no visible or detectable amount of aggregates, a FVIII monomer content of >98% (mean value for the 5 batches of 98.6%) and fragment content of <2% (mean value for the 5 batches of 1.4%). The size exclusion eluate, after performing the affinity step followed by the anion exchange step and the size exclusion step, shows a high content of Factor VIII monomer, no detectable or visible signs of aggregate and low content of FVIII fragments.

CONCLUSION EXAMPLE 4

All three chromatography steps performed in sequence 1-3 according to example 4, contributes to the removal of inactive Factor VIII molecules, according to the invention. This indicates that the inactive Factor VIII molecules removed trough the different steps are different in its biophysical properties and performing the steps in sequential conjunction with each other to provide a final purified Factor VIII product with the lowest degree of inactive Factor VIII content and the highest degree of Factor VIII monomer content would give the lowest risk of immunogenic reactions in patients.

EXAMPLE 5

Size Exclusion Chromatography Parameters (Column Height, FVIII:C Concentration, Load)

The following example illustrates size exclusion parameters (FVIII:C concentration and column load) importance for the biological activity (FVIII:C/Ag).

Column and Resin

A BPG200 column was packed with Superdex 200 p.g. resin to a bed height of 62 cm giving a column volume of 19.5 litres. The Superdex 200 p.g. resin was obtained from GE Healthcare (Cat. No. 17-1043).

Starting Material

A Factor VIII containing material with the following composition, 0.4 mol/kg NaCl, 0.02 mol/kg $CaCl_2$, 0.02 mol/kg L-histidin, 0.02% (w/w) Polysorbat 80, pH 6.2 was used as starting material. The starting material was produced as described in example 2 (the product elution fraction).

Buffer Composition:

Equilibration Buffer 30.7 g/kg NaCl, 0.5 g/kg $CaCl_2$, 2.0 g/kg sodium citrate, 9.2 g/kg arginine, 9.2 g/kg sucrose, 0.02% (w/w) Polysorbate 80, pH: 7.0±0.1, conductivity: 49±2 mS/cm at +25° C.

The equilibration is not limited to the stated pH, concentrations, and type of buffer, salts or detergent.

Seven different batches (A-G) were performed according to Table 8 below. The column was equilibrated with equilibration buffer followed by specified loading of the starting material. The resin was thereafter subjected to equilibration buffer to allow the Factor VIII solution to separate over the size exclusion column. When the absorbance at 280 nm was raised over 0.035 AU at the outlet of the column, the collection of the eluate was started and when the absorbance was decreased to 0.005 AU the collection of the eluate was stopped. Samples were taken from the starting material and the eluate and analyzed in regard of FVIII:C, FVIII:Ag and SEC-HPLC1.

TABLE 8

Experimental conditions and resulting biologic activity FVIII:C/Ag

| Batch | FVIII:C load concentration, IU/mL | Column load, % | Biologic activity, FVIII:C/Ag starting material | Biologic activity, FVIII:C/Ag eluate |
|---|---|---|---|---|
| A | 17101 | 5.5 | na | 0.90 |
| B | 16685 | 5.3 | 0.83 | 0.81 |
| C | 18046 | 5.0 | 0.95 | 0.99 |
| D | 21445 | 5.2 | 0.97 | 1.01 |
| E | 15925 | 4.3 | 0.86 | 0.81 |
| F | 14844 | 1.9 | 0.92 | 0.79 |
| G | 9149 | 3.9 | 0.91 | 0.82 |

Table 8 illustrates that the removal of inactive Factor VIII forms from the starting material over the size exclusion step is depending on different parameters. A relatively low Factor VIII:C concentration in combination with a relatively low load on the column, as in batch E (15925 IU/mL, 4.3%) F (14844 IU/mL, 1.9% and G (9149 IU/mL, 3.9%), seems to be negative for the biological activity, as measured with the ratio FVIII:C/FVIII:Ag, in the respectively eluates (E-0.81, F-0.79, G-0.82), as compared to batch A-D (A-0.90, B-0.81, C-0.99 and D-1.01)

CONCLUSION EXAMPLE 5

The FVIII:C concentration in combination with the column load is parameters of importance for the outcome of the size exclusion step in regard of biological activity. Based on data described in example 3 and example 4, both using the bed height 69 cm, it seems that the results as described in example 5 with a slightly lower bed height (62 cm), probably in combination with the two other factor's of importance (FVIII:C concentration and column load) also affect the outcome of the size exclusion step. It is shown that the size exclusion step works better with a high Factor VIII:C concentration, a high column bed height and a column load of ≥4%.

EXAMPLE 6

Stability of Biologically Active Monomeric Factor VIII in Frozen State

The following example illustrates the stability of a biologically active monomeric Factor VIII solution processed according to example 4, in frozen state.

Starting Material

A Factor VIII solution produced according to example 4, with a Factor VIII monomer content of >99%, an aggregate content of <1% and an amount of inactive Factor VIII of >0.9, as measured with the ratio of biologically active Factor VIII in relation to the total amount of Factor VIII (FVIII:C/FVIII:Ag)

Factor VIII Buffer Environment:

30.7 g/kg NaCl, 0.5 g/kg $CaCl_2$, 2.0 g/kg sodium citrate, 9.2 g/kg arginine, 9.2 g/kg sucrose, 0.02% (w/w) Polysorbate 80, pH: 7.0±0.1, conductivity: 49±2 mS/cm at +25° C.

Freezing and Storage Conditions:

The Factor VIII solution is filled in a plastic low density polyethylene container and frozen down to −40° C. through a fast freezing process during maximum 60 minutes. The frozen solution is thereafter stored at a temperature between −60° C. and −80° C. for 36 months. Samples are taken after 0, 6, 9, 12, 18, 24 and 36 months storage and analyzed for biological activity and monomer, aggregate, fragment content.

TABLE 9

Stabilty of Factor VIII solution stored frozen in a temperature between −60° C. and −80° C.

| Analyze | 0 month | 6 months | 9 months | 12 months | 18 months | 24 months | 36 months |
|---|---|---|---|---|---|---|---|
| Biological Activity (FVIII:C, IU/mL) Factor VIII | 5196 | 5150 | 5962 | 5132 | 5989 | 5220 | 5317 |
| monomer | >94% | >94% | >94% | >94% | >94% | >94% | >94% |
| aggregate | <3% | <3% | <3% | <3% | <3% | <3% | <3% |
| fragment (SEC-HPLC1) | <3% | <3% | <3% | <3% | <3% | <3% | <3% |

As can be seen in Table 9, the Factor VIII solution is completely stable for at least 36 months storage at temperature between −60° C. and −80° C., in regard of biological activity and Factor VIII monomeric content (aggregate and fragment formation).

EXAMPLE 7

Stability of Biologically Active Monomeric Factor VIII in a Freeze-Dried Product The following example illustrates the stability of a biologically active monomeric Factor VIII solution processed according to example 4 and example 6 and thereafter freeze dried.

Starting Material

A frozen Factor VIII solution produced according to example 4 and example 6, with a Factor VIII monomer content of >99%, an aggregate content of <1% and an amount of inactive Factor VIII of >0.9, as measured with the ratio of biologically active Factor VIII in relation to the total amount of Factor VIII (FVIII:C/FVIII:Ag).

Content of one vial Factor VIII after freeze-drying:

| | |
|---|---|
| Sucrose | 13.5 mg |
| Arginine hydrochloride | 13.5 mg |
| Poloxamer 188 | 3 mg |
| Sodium Chloride | 45 mg |
| Calcium Chloride dihydrate | 0.75 mg |
| Sodium Citrate dihydrate | 3 mg |
| Biologically active Factor VIII | 250 IU |

Freeze-Drying Procedure:

2.5 mL of the Factor VIII starting material is filled in a 8 mL moulded glass vial (type I) to a total amount of Factor VIII of 250 IU. The vial is subjected to a freeze-drying process as described in Table 10.

TABLE 10

| Freeze-drying process | |
|---|---|
| 1. Freezing | Ramp from room temperature to −5° C. in 30 min |
| | Hold at −5° C. for 30 min |
| | Ramp from −5° C. to −55° C. in 1 h |
| | Hold at −55° C. for 2 h |
| 2. Annealing | Ramp from −55° C. to −25° C. in 1 h 15 min |
| | Hold at −25° C. for 4 h |
| | Ramp from −25° C. to −40° C. in 1 h 15 min |
| | Hold at −40° C. for 2 h |
| 3. Primary Drying | Reduce pressure to 0.065 mbar |
| | Ramp from −40° C. to −30° C. in 30 min |
| | Hold at −30° C. for 42 h |
| 4. Secondary Drying | Reduce pressure to 0.02 mbar |
| | Ramp from −30° C. to +25° C. in 4 h |
| | Hold at +25° C. for 6 h |

After the freeze-drying process, the vials are closed with bromobutyl stoppers and capsulated with aluminium caps. The vials were stored at +5° C. for 24 months. Samples were taken after 0, 6, 9, 12, 18 and 24 months storage by reconstitution of the freeze-dried product in 2.5 mL of water for injection and to thereafter analyzed for biological activity and monomer, aggregate, fragment content, see Table 11.

TABLE 11

Stability of a freeze-dried Factor VIII solution stored at +5° C.

| Analyze | 0 month | 6 months | 9 months | 12 months | 18 months | 24 months |
|---|---|---|---|---|---|---|
| Biological Activity (FVIII:C) Factor VIII | 267 IU | 280 IU | 280 IU | 281 IU | 287 IU | 282 IU |
| monomer | >94% | >94% | >94% | >94% | >94% | >94% |
| aggregate | <3% | <3% | <3% | <3% | <3% | <3% |
| fragment (SEC-HPLC1) | <3% | <3% | <3% | <3% | <3% | <3% |

As can be seen in Table 11, the freeze-dried Factor VIII product is completely stable for at least 24 months storage at temperature at +5° C., in regard of biological activity and Factor VIII monomeric content (aggregate and fragment formation).

EXAMPLE 8

Determination of FVIII C/Ag ration and aggregate, monomer and fragment in the final freeze-dried product according to the invention and comparing it with recombinant products using different purification methods.

The following example illustrates the superior properties of the product according to the invention and comparing it with other commercially available recombinant products using different purification methods.

Starting Material

A freeze-dried Factor VIII product produced according to example 7 of the invention, was reconstituted and compared to 3 different competitor rFVIII products purified according to 3 different purification methods (A-C) and stabilized with different formulation buffers. At least 1 vial strengths (250 IU, 1000 IU or 3000 IU) were analysed for a good comparison between different formulation compositions in regard stabilizers/FVIII. All samples were analysed for FVIII C/Ag and for aggregate, monomer and fragment according to the SEC-HPLC2 analytical method, under native running conditions.

TABLE 1

| | FVIII/ vial, IU | FVIII:C, IU/mL | FVIII:Ag, IU/mL | C/Ag | SEC-HPLC2, % | | |
|---|---|---|---|---|---|---|---|
| | | | | | Aggregate | Monomer | Fragment |
| rFVIII acc. to pur. meth. A | 250 | 95 | 132 | 0.72 | 0 | 76 | 24 |
| rFVIII acc. to pur. meth. A | 1000 | 441 | 573 | 0.77 | 0 | 76 | 24 |
| rFVIII acc. to pur. meth. A | 3000 | 638 | 925 | 0.69 | 0 | 76 | 24 |
| rFVIII acc. to pur. meth. B | 1000 | 242 | 263 | 0.92 | 0 | 99 | 1 |
| rFVIII acc. to pur. meth. C | 500 | 104 | 130 | 0.8 | 0 | 77 | 23 |
| rFVIII acc. to pur. meth. C | 1000 | 205 | 270 | 0.76 | 0 | 80 | 20 |

TABLE 1-continued

|  | FVIII/vial, IU | FVIII:C, IU/mL | FVIII:Ag, IU/mL | C/Ag | SEC-HPLC2, % | | |
|---|---|---|---|---|---|---|---|
|  |  |  |  |  | Aggregate | Monomer | Fragment |
| rFVIII acc. to pur. meth. C | 3000 | 600 | 732 | 0.82 | 0 | 77 | 23 |
| rFVIII acc. to pur. met. of inv. | 250 | 119 | 131 | 0.91 | 0 | 100 | 0 |
| rFVIII acc. to pur. met. of inv. | 1000 | 494 | 531 | 0.93 | 0 | 100 | 0 |

CONCLUSION EXAMPLE 8

Table 1 shows the superior quality for recombinant FVIII produced according to the invention on a purified and freeze-dried product, in regard of 100% monomer content and a FVIII C/Ag ration >0.9. This implicate no or very little amount of non biological active Factor VIII in the final product compared to competitor all purified and stabilised under different conditions.

EXAMPLE 9

Comparing inhibitor formation in previous untreated haemophilia A patients of a rFVIII product purified, formulated, freeze-dried and stored according to the invention, comparing it with published data for one competitor recombinant FVIII product[21]. And as well comparing FVIII C/Ag ration and aggregate, monomer and fragment between the two products.

The following example illustrates the superior properties of the product according to the invention and comparing it with one commercially available recombinant FVIII product available on the market.

Starting Material

A freeze-dried Factor VIII product produced according to example 7 of the invention, was compared to one competitor rFVIII product commercially available on the market, purified according to method A as described in example 8. The two products were given to the patients and followed for inhibitor formation development, according to standard clinical protocols[21] for previous untreated haemophilia A patients. The amount of the patients developing inhibitors for respectively product as well as the Factor VIII C/Ag ratio and aggregate/monomer/fragment profile can be seen in Table 2.

CONCLUSION EXAMPLE 9

Table shows a significantly lower amount of inhibitors detected in previous untreated haemophilia A patients using the product of the invention compared with one commercially available rFVIII product on the market. In addition Table 10 shows the Factor VIII C/Ag ratio and the aggregate/monomer/fragment profile of examples of respectively products for 2 (250 IU and 1000 IU) respectively 3 (250 IU, 1000 IU and 3000 IU) different vial strengths. It could be hypothesized that a lower amount of biological inactive FVIII in the product would decrease the amount of inhibitor formed in patients. Thus, implicating the importance of purification, stabilisation, freeze-drying and storage for recombinant FVIII products to minimize patient risk in regard of immunological reactions.

EXAMPLE 10

Specific activity (purity) of a recombinant FVIII product purified according to the invention.

The following example illustrates the excellent purity of a recombinant FVIII product purified according to the invention.

Starting Material

A frozen Factor VIII solution produced according to example 4 and example 6, with a Factor VIII monomer content of >99%, an aggregate content of <1% and an amount of inactive Factor VIII of >0.9, as measured with the ratio of biologically active Factor VIII in relation to the total amount of Factor VIII (FVIII:C/FVIII:Ag) was analysed according to FVIII:C and total protein content according to Bradford.

TABLE 2

|  | FVIII/vial, IU | FVIII:C, IU/mL | FVIII:Ag, IU/mL | C/Ag | SEC-HPLC2, % | | | Previously untreated patients (PUP's) Inhibitors, % (n = amount of total treated patients) |
|---|---|---|---|---|---|---|---|---|
|  |  |  |  |  | Aggregate | Monomer | Fragment |  |
| rFVIII acc. to pur. meth. A | 250 | 95 | 132 | 0.72 | 0 | 76 | 24 | 35.2 (128)* |
| rFVIII acc. to pur. meth. A | 1000 | 441 | 573 | 0.77 | 0 | 76 | 24 |  |
| rFVIII acc. to pur. meth. A | 3000 | 638 | 925 | 0.69 | 0 | 76 | 24 |  |
| rFVIII acc. to invention | 250 | 119 | 131 | 0.91 | 0 | 100 | 0 | 11.6 (43)** |
| rFVIII acc. to invention | 1000 | 494 | 531 | 0.93 | 0 | 100 | 0 |  |

*Published studyCollins2014[21],
**On-going study unpublished data

CONCLUSION EXAMPLE 10

Figure 18:
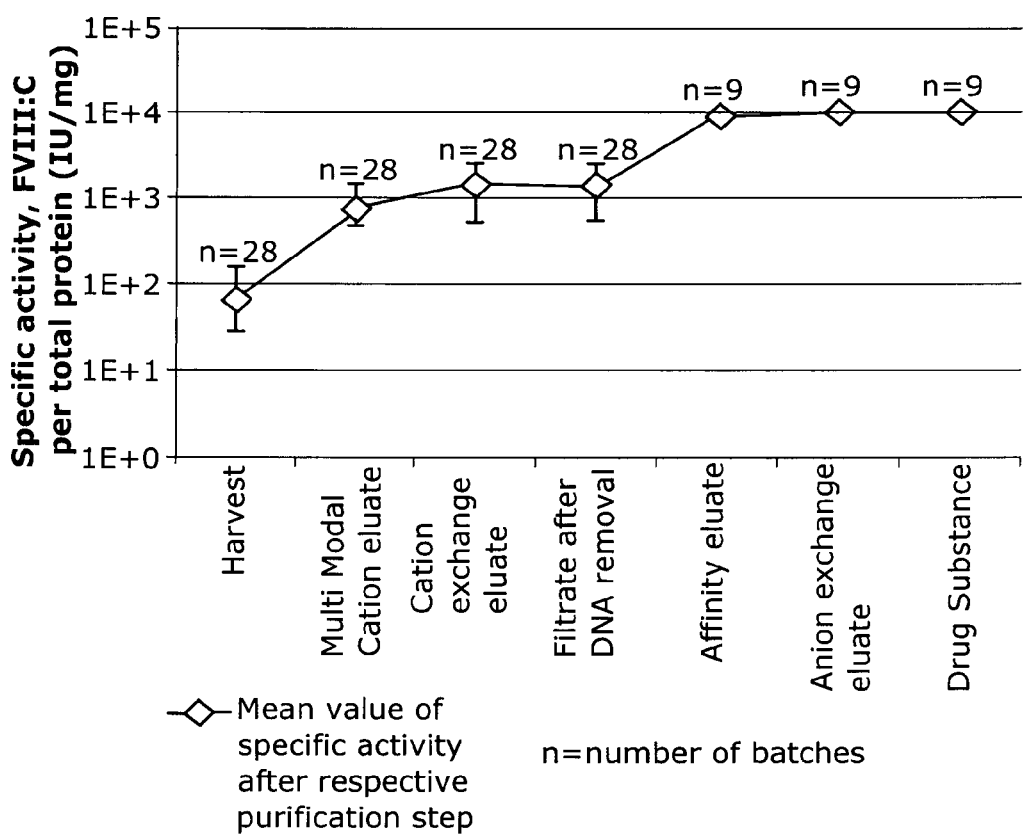
FIG. 18: Increase of the purity of Factor VIII during the purification processes of the invention.
Figure 19:
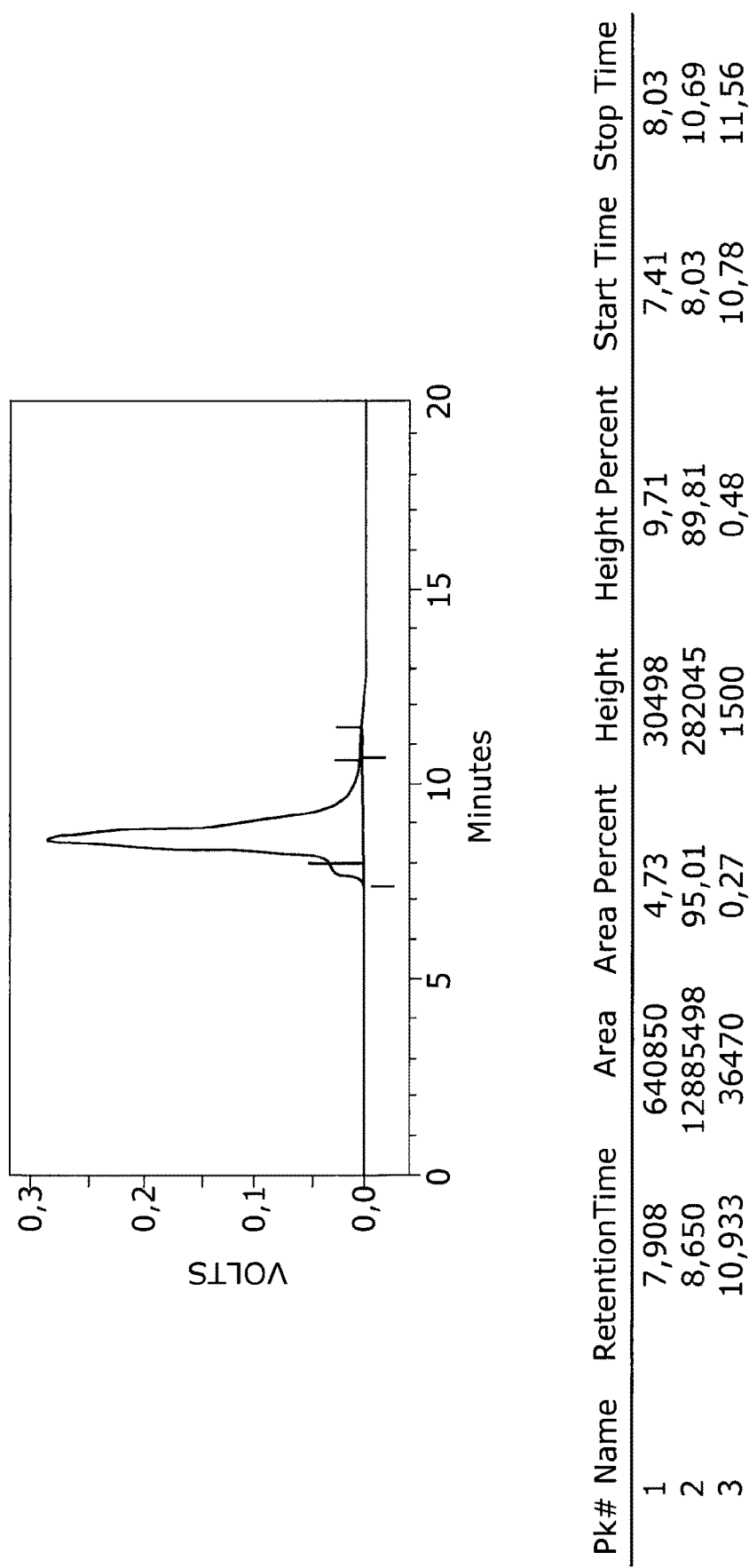
FIG. 19: A chromatogram from an analytical size exclusion chromatography column (SEC-HPLC2) showing the chromatographic profile from a sample prepared according to example 7 (purified and freeze-dried according to the invention) and it's respectively aggregate, monomer and fragment content in percentage after reconstitution of the freeze dried product (1000 IU vial). The monomer content of this sample is in principle 100% (the slight shoulder on left on the monomer peak is, based on the molecular weight standard retention curve (FIG. 23) to be included in the FVIII monomer peak) and eluting at approximately 7-10 minutes in the SEC-HPLC2 chromatogram, with no visible signs of aggregates and fragments.
Figure 20:
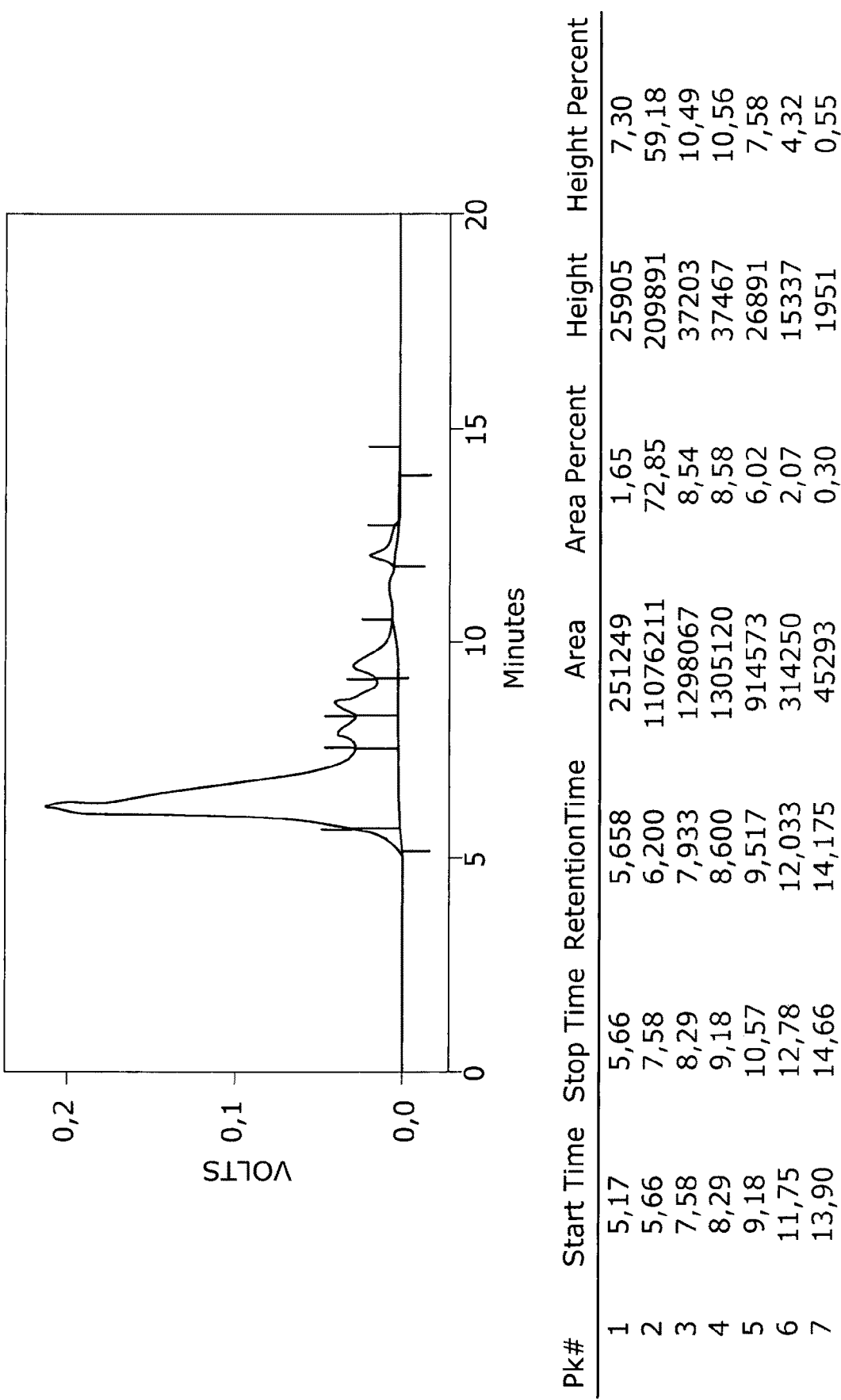
FIG. 20: A chromatogram from an analytical size exclusion chromatography column (SEC-HPLC2) showing the chromatographic profile from a sample prepared according to Purification method A[22] and freeze-dried and it's respectively aggregate, monomer and fragment content in percentage after reconstitution of the freeze dried product (1000 IU vial). The monomer content of this sample is approximately 76% with no visible signs of aggregates and approximately 24% fragments. The rFVIII product is a full length FVIII product with intact B-domain with an approximate molecular weight of 300 kD, which gives a monomer FVIII elution in the SEC-HPLC2 chromatogram at approximately 5-8 minutes. The fragment peak is calculated starting directly after the monomer peak at approximately 8-13 minutes.
Figure 21:
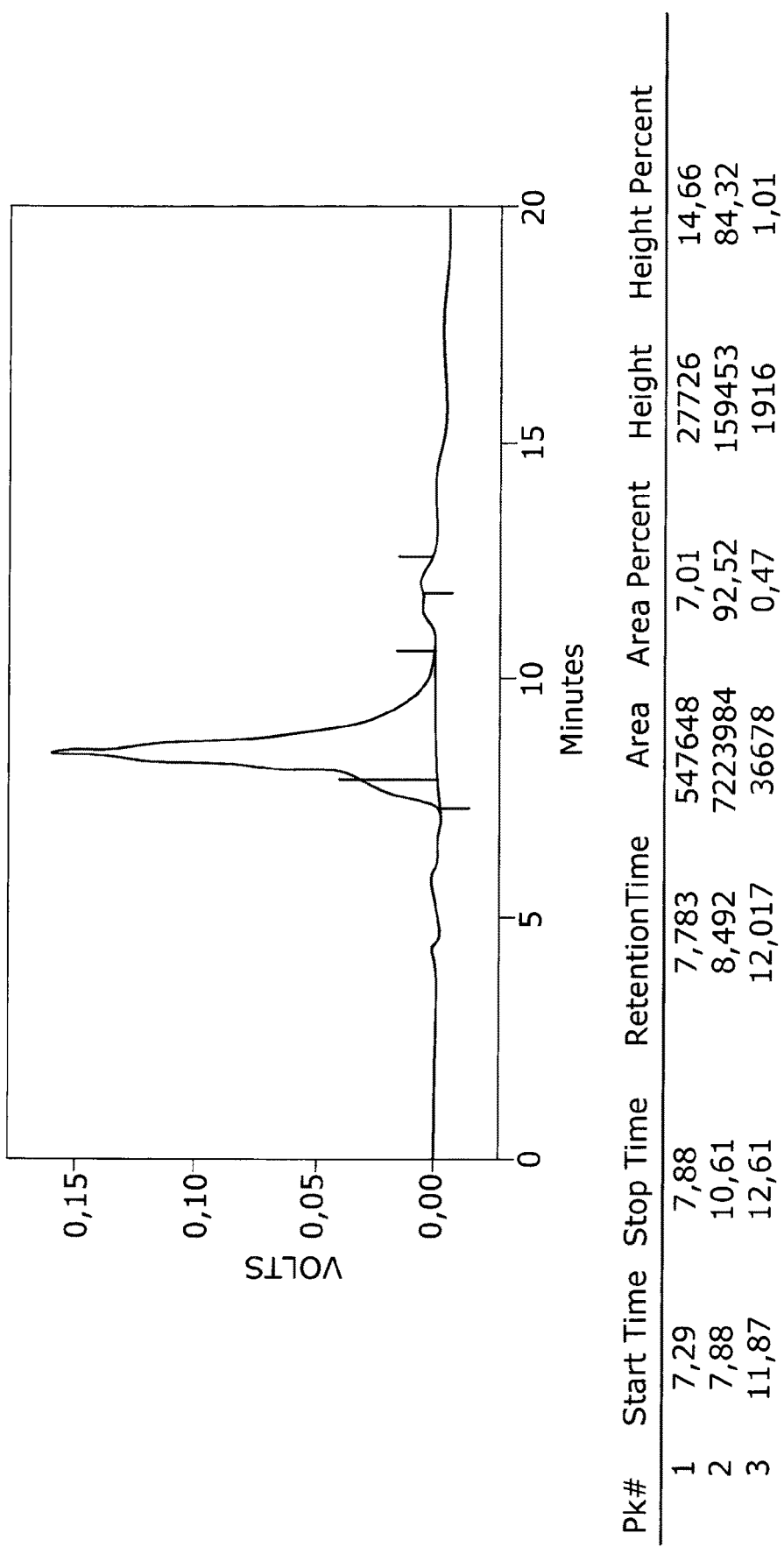
FIG. 21: A chromatogram from an analytical size exclusion chromatography column (SEC-HPLC2) showing the chromatographic profile from a sample prepared according to Purification method B[22] and freeze-dried and it's respectively aggregate, monomer and fragment content in percentage after reconstitution of the freeze dried product (1000 IU vial). The monomer content of this sample is approximately 99% (the slight shoulder on left on the monomer peak is, based on the molecular weight standard retention curve (FIG. 23) to be included in the FVIII monomer peak) with no visible signs of aggregates and approximately 1% fragments. The rFVIII product is a B-domain deleted FVIII product with an approximately molecular weight of 170 kD, which gives a monomer FVIII elution in the SEC-HPLC2 chromatogram at approximately 7-10.5 minutes. The fragment peak is calculated starting directly after the monomer peak at approximately 10.5-13 minutes.
Figure 22:
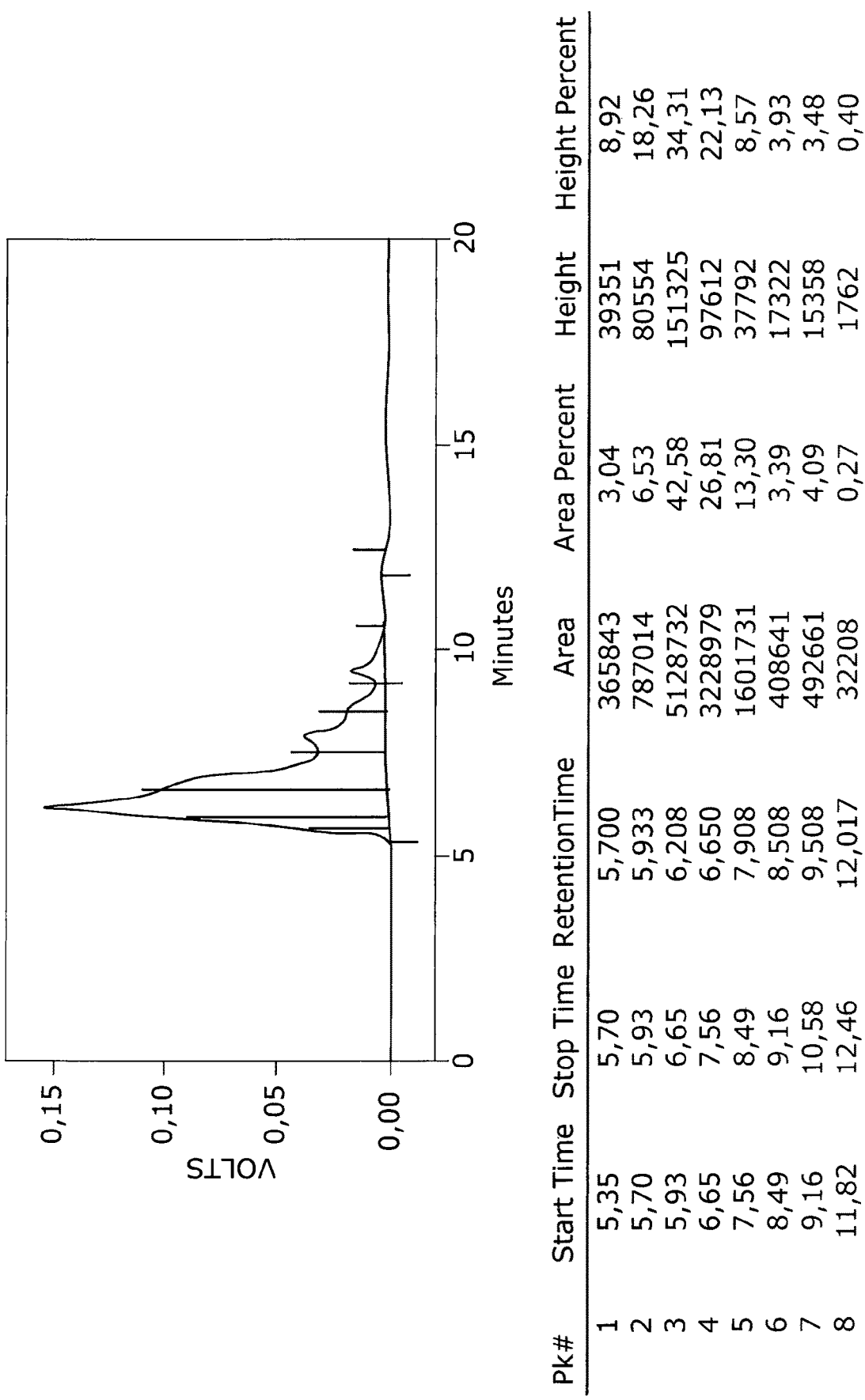
FIG. 22: A chromatogram from an analytical size exclusion chromatography column (SEC-HPLC2) showing the chromatographic profile from a sample prepared according to Purification method C[22] and freeze-dried and it's respectively aggregate, monomer and fragment content in percentage after reconstitution of the freeze dried product (1000 IU vial). The monomer content of this sample is approximately 80% with no visible signs of aggregates and approximately 20% fragments. The rFVIII product is a full length FVIII product with intact B-domain with an approximate molecular weight of 300 kD, which gives a monomer FVIII elution in the SEC-HPLC2 chromatogram at approximately 5-8 minutes. The fragment peak is calculated starting directly after the monomer peak at approximately 8-13 minutes.
Figure 23:
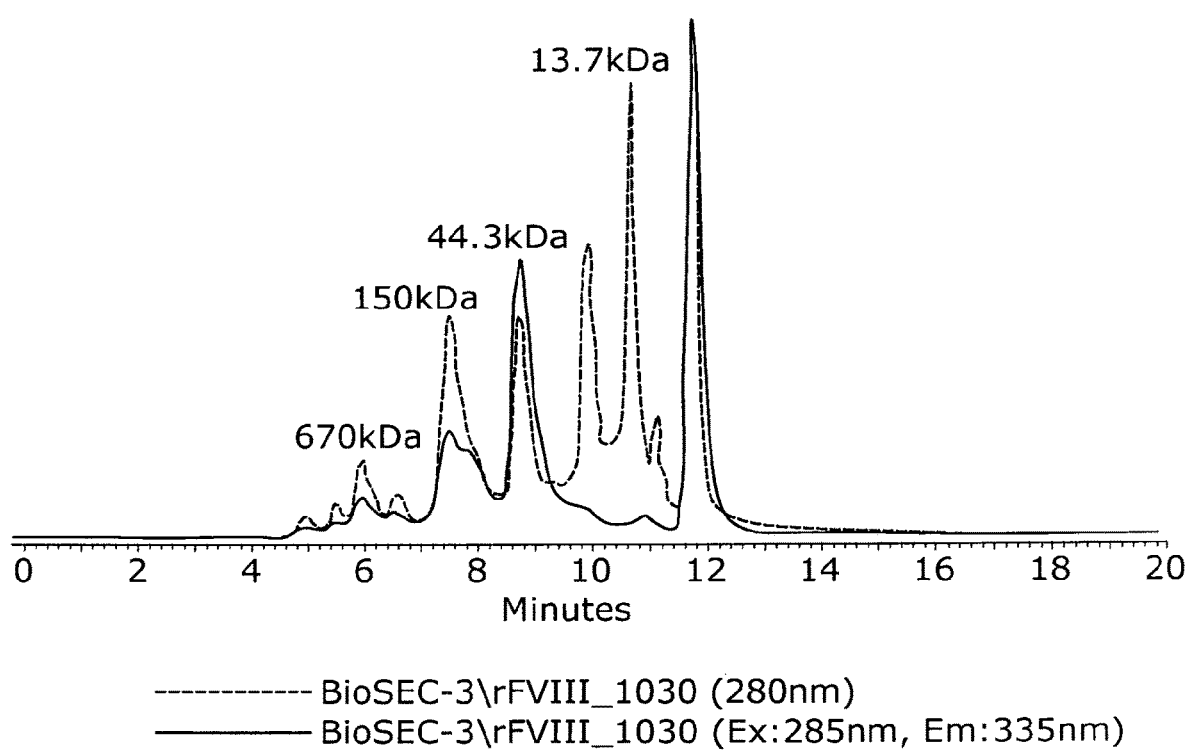
FIG. 23: A chromatogram from an analytical size exclusion chromatography column (SEC-HPLC2) showing the chromatographic profile from a molecular weight standard sample (15-600 kD, 69385, Sigma-Aldrich Chemie GmbH).

FIG. 18 shows the increase of the purity as measured by FVIII:C/mg protein (as measured with Bradford) for 9 batches as purified according to the invention (the 3 last steps; affinity eluate, anion exchange eluate and the Drug substance (=size exclusion chromatography eluate)) in production scale, ending up with a purity of in the range of 10 000 IU/mg protein, which is essentially pure rFVIII.

Description of Analysis

Factor VIII biologic activity (FVIII:C) is measured with a chromogenic assay (COATEST SP FVIII kit, 82 4086 63, Chromogenix/Instrumentation Laboratory (US)), based on a two-stage photometric method that measures the biological activity of factor VIII as a cofactor.[17]

The amount of Factor VIII antigen content (FVIII:Ag) is measured with a ELISA kit (ASSERACHROM® VIII:Ag, enzyme immunoassay for Factor VIII, kit, Diagnostica Stago (France), as further described[18] with replacement of the provided kit buffer with Tris-NaCl buffer+1% bovine serum albumin for sample dilutions.

Factor VIII monomer, aggregate and fragment was measured using two different size exclusion size exclusion chromatography (SEC-HPLC) analytical columns (SEC-HPLC 1,Superdex 200, 10/300 GL, GE Healthcare and SEC-HPLC2, BioSEC-3, Agilent Technologies)

SEC-HPLC1 method(Superdex 200) processed under native buffer conditions (25 mM HEPES, 0.5M NaCl, 0.3M arginine, 50 mM $CaCl_2$, 0.02% Polysorbate 80, pH 7.5). Sample load is approximately 1% of the size exclusion column and the Factor VIII:C concentration is approximately 1000 IU/ml. Monomer was defined as the main FVIII chromatogram peak, aggregate as the peak eluting before and fragment as the chromatogram peak eluting after the FVIII monomer peak.

SEC-HPLC2 method (BiSEC-3) Recombinant expressed FVIII samples, were analysed with respect to their composition of FVIII aggregates, monomers and fragments using size exclusion chromatography (BioSEC-3, 30×4.6 mm SEC column Agilent Technologies) under non-denaturing buffer conditions (25 mM Tris-HCl, 50 mM $CaCl_2$, 500 mM NaCl; pH 7.0) at a flow rate of 0.4 mL/min on a Shimadzu HPLC system. Sample load was approximately 0.2-0.4 μg according to determined FVIII activity (FVIII:C) values. Monomer was defined as the main FVIII chromatogram peak, aggregate as the peak eluting before and fragment as the chromatogram peak eluting after the FVIII monomer peak. The retention time for analysed rFVIII samples were as well compared with the retention time of a molecular weight sample (15-600 kD, 69385, Sigma-Aldrich Chemie GmbH) Factor VIII degeneration product based on size is measured using FVIII Western Blot. FVIII molecular mass distribution proteins and peptides in factor VIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane which is subsequently incubated with a blocking agent. Commercial available polyclonal sheep antibodies directed to the whole human factor VIII molecule is then added followed by a secondary enzyme-labelled antibody as a probe. As a third step a chemiluminescent substrate is added and when combined with the enzyme, light is produced as a by-product. The light output is captured as a real time image using a cooled Charge-Coupled Device camera. The intensity of the signal is correlated with the abundance of the antigen (FVIII) on the blotting membrane.

2D-Electrophoresis with Silver Staining was carried out in order to study the electrophoretic band pattern of the Factor VIII protein chain. Isoelectric focusing was performed as the first dimension run using a linear pH gradient of pH 3 to 10. The second dimension SDS-PAGE was run using Tris-Acetate (3-8%) gels. The gels were stained with silver-stain following the second dimension run.

Amino acid composition analysis was performed through-_compositional amino acid analysis following acid hydrolysis of the protein. The proteins were hydrolysed in 6M HCl at 110° C. for 24 h and thereafter the amino acids are separated by cation exchange chromatography on sulfonated polystyrene resins and detected continuously in the eluent. The detection is based on post column ninhydrin derivatisation using a dual photometer for simultaneous measurement at 440 nm for proline and 570 nm for all other amino acids. No values from cysteine or tryptophane can be measured as this method does not measure these residues properly. Values for lysine and arginine were also omitted because of the interference of lysine and arginine present in the buffer formulation.

N-Glycan finger printing was performed by High-performance anionic exchange chromatography with pulsed amperometric detection (HPAEC-PAD), to determine N-linked glycans.[19] The N-linked glycan chains are released from the proteins by enzymatic cleavage (N-Glycanase Plus, product No GKE-5010B, from Prozyme) and subsequently bound to the anion exchange chromatography column at high pH (pH 13), followed by a gradient with increased ionic strength and decreased pH. The separation of the various glycan chains in the chromatography system is achieved due to differences in charge, size, and structure. The anionic exchange column was a CarboPac™ PA 200 chromatography column (250 mm×3 mm ID, particle size 5.5 μm, product No 062896) from Dionex and CarboPac™ PA 200 guard column (50×3 mm ID, product No 062895) from Dionex. The detection system used was an ICS-3000 CD electrochemical detector with a 3 mm gold membrane (ICS-3000 Au Working Electrode, 3 mm, product No 063723), controlled by the software Chromeleon.

Samples corresponding to the different chromatographic peaks were collected in fractions with each fraction corresponding to a retention time of 1 min. The glycans were desalted on porous graphitic carbon columns and thereafter each fraction was concentrated. Chromatographic separation was performed on a capillary LC-system, using a PGC-column, and the glycans were electrosprayed online to a time of flight MS. A database from Functional Glycomics [www.functionalglycomics.org] was used by typing in the masses and searching for a possible match. Because of the high mass accuracy (about 30 ppm) the identification of respectively glycans was determined to be accurate.

Trypsin peptide fingerprint mapping was performed including two main steps. In the first step trypsin is used to digest the protein to be analysed into polypeptides, which are in a second step separated and recorded using HPLC-technology. By this way a specific pattern ("fingerprint") is generated. The peptides are detected by their fluorescence (mainly thryptophane) yielding a more simplified map compared to UV detection. The recorded fluorescence pattern over time represents the peptide map for the analysed sample.

Protein concentration was determined using the Bradford assay[23].

VIIISelect is an affinity chromatography medium (resin) designed for the purification of recombinant B-domain-depleted factor VIII.

According to the data file 28-9662-37 AB, GE healthcare key characteristics of VIIISelect include:

Efficient purification of recombinant B-domain-deleted factor VIII, with high yields and retained specific activity High selectivity Excellent scalability Animal-free production Efficient purification processes of recombinant blood coagulation factors are needed for treating hemophilia patients. VIIISelect is an affinity chromatography medium designed for the purification of recombinant B-domain-depleted factor VIII, a key recombinant blood factor used for the treatment of Hemophilia A. Due to the sensitive nature of the factor VIII molecule, it is important to limit the number of steps in the downstream process. The high selectivity and yield obtained using VIIISelect enables a robust and efficient purification process with excellent purity obtained in one step. Animal-free production and low ligand leakage are additional properties that make this medium highly suitable for large-scale production of recombinant B-domain-depleted factor VIII. VIIISelect is part of GE Healthcare's Custom Designed Media program.

Medium Characteristics

VIIISelect is based on highly cross-linked agarose base matrix, which enables rapid processing of large sample volumes. The ligand, a 13 kD recombinant protein, is attached to the porous base matrix via a hydrophilic spacer arm making it easily available for binding to recombinant domain-depleted factor VIII (FIG. 1). Table 1 summarizes the main characteristics of VIIISelect.

Functional Principles

Affinity chromatography exploits an immobilized ligand that adsorbs a specific molecule or group of molecules under suitable binding conditions and desorbs them under suitable elution conditions. These conditions depend on the target molecule, feed composition, and chromatography medium, and must be studied together with other chromatographic parameters (e.g., sample load, flow velocity, bed height,

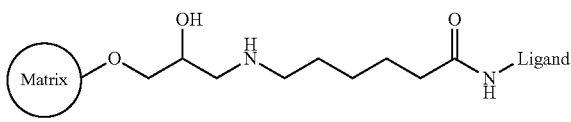

Partial structure of VIIISelect.

regeneration, and cleaning-in-place) to establish the conditions that will bind the target molecule with the highest product recovery.

Recombinant factor VIII can be applied directly to the VIIISelect column from clarified cell lysates or supernatants.

TABLE 1

Main characteristics of VIIISelect

| | |
|---|---|
| Matrix | highly cross-linked agarose |
| Average particle size | 75 μm |
| Ligand | Recombinant protein ($M_r$ 13 000) produced in *S. cerevisiae*. |
| Capacity | Typically 20 000 IU/ml gel |

TABLE 1-continued

Main characteristics of VIIISelect

| | |
|---|---|
| Recommended flow rate | Up to 300 cm/h at 30 cm bed height |
| Maximum back pressure | 0.3 MPa, 3 bar |
| pH stability | |
| Long term | 3-10 |
| Short term | 2-12 |

Buffers should always contain $Ca^{2+}$ ions in order to promote formation of the active conformation of factor VIII. The presence of a surfactant is needed to inhibit surface-induced denaturation/adsorption. Neutral pH buffers and histidine should always be used for binding, washing, and elution for maintaining the specific factor VIII activity. Depending on the nature of the applied material to VIIISelect, regeneration is normally needed after each cycle, followed by re-equilibration in equilibration/loading buffer.

Stability

The ligand is linked to the highly cross-linked base matrix via a stable amide bond. FIG. 2 shows a study where VIIISelect was stored at room temperature at different pH values for one week. The figure shows that the stability is high between pH 3 and 10. GE recommend long term storage between pH 3 and 10, and short term storage pH 2 and 12.

Storage

The recommended storage conditions are 20% ethanol at 4° C. to 8° C. VIIISelect is supplied pre-swollen in a 20% ethanol solution.

Cleaning-in-Place

A cleaning protocol for VIIISelect may consist of 0.1 M citric acid or 0.5 M phosphoric acid. However, prolonged exposure to pH <2 should be avoided due to decomposition of the agarose base matrix. Sodium hydroxide (0.01 M) can be used alone or in combination with sodium sulfate/chloride as stabilizer.

REFERENCES

1. Wang etal., Coagulation Factor VIII; structure and stability, International Journal of pharmaceutics 259 (2003) 1-15.

2. Svensson etal., Evaluation of the metal binding site in a recombinant coagulation factor VIII identifies two sites with unique metal binding sites, Biological Chemistry, DOI: 10.1515/hsz-2012-0298

3. Peerlinck etal., Factor VIII inhibitors in previous treated Haemophilia A patientse with a double virus inactivated plasma derived Factor VIII concentrate, Thrombosis and Haemostasis 77 (1) 80-86 (1997).

4. Fang etal., The protein structure and effect of Factor VIII, Thrombosis Research (2007) 119, 1-13.

5. Lin etal., Relationship between Factor VIII:Ag and Factor VIII in recombinant and plasma derived Factor VIII concentrate, Haemophilia (2004), 10, 459-469.

6. Mire-Sluis etal., Analysis and immunogenic potential of aggregates and particles, Bioprocess International 9(11) December 2011 38-43.

7. Grillo etal., Conformational origin of the aggregation of recombinant human Factor VIII, Biochemistry 2001, 40, 586-595.

8. Wang etal., Correlation with rFVIII inactivation with aggregation in solution, Pharmaceutical Research, Vol. 20, No. 4, April 2003.

9. Thim etal., Purification and characterization of new recombinant Factor VIII (N8), Haemophilia (2010), 16, 349-359.

10. Kelley etal., Development and validation of ab affinity chromatography step using a peptide ligand for cGMP production of Factor VIII, Biotechnology and Bioengineering, Vol. 87, No. 3, Aug. 5, 2004.

11. McCue etal., Application of a novel affinity adsorbent for the capture and purification of recombinant Factor VIII compounds, Journal of Chromatography A, 1216 (2009) 7824-7830.

12. Kusch etal., Factor VIII assay mimicking in vivo coagulation conditions, Haemophilia (2013), 1-7.

13. Sommer etal., Comparative field study evaluating activity of recombinant FVIII Fc fusion protein in plasma samples at clinical haemostatis laboratories, Heamophilia (2013) 1-7.

14. Muyldermans, Single domain camel antibodies: current status, Reviews in Moleculer Biotechnology 74, (2001), 277-302.

15. Fay, Factor VIII: Function and structure, International Journal of Hematology 83 (2006) 103-108.

16. Metal ion-independent association of Factor VIII subunits and the roles of calcium and copper ions for cofactor activity and inter-sub-unit affinity, Biochemistry 2001, 40, 10293-10300.

17. Rosen, Assay of Factor VIII:C with a chromogenic substrate, Scand J Haemetol-Suppl 40, Vol. 33, 1984, 139-145.

18. Girma etal., Assay of Factor VIII antigen (FVIII:CAg) in 294 Haemophilia A patients by a new commercial ELISA using monoclonal antibodies, (Haemophilia 1998), 4, 98-103.

19. Cataldi etal., Carbohydrate analysis by high performance anion-exchange chromatography with pulsed amperometric detection: the potential is still growing, Fresenius J Anal Chem 2000; 368:739-58.

20. Casademunt et al., The first recombinant human coagulation factor VIII of human origin: human cell line and manufacturing characteristics. Eur J Haematol. 2012; 89(2): 165-76.

21. Collins etal., Factor VIII brand and the incidence of factor VIII inhibitors in previously untreated UK children with severe haemophilia A, 2000-2011, Bloodjournal.org, DO1 10.1182/blood-2014-07-580498

22. Boedeker, Production processes of licensed recombinant factor VIII preparations, Seminars in thrombosis and hemostasis volume 27, number 4, 2001.

23. Bradford MM. A rapid and sensitive method for the quantitation of microgram quantities of protein utilizing the principle of protein-dye binding. Anal Biochem. 1976; 72:248-54.

The invention claimed is:

1. A process for manufacturing a Factor VIII product having a ratio of FVIII:C/FVIII:Ag of at least 0.7 in the Factor VIII product comprising at least one chromatographic step employing an affinity chromatography resin having an affinity for specifically binding of Factor VIII which is effected by an affinity ligand which is immobilised on the affinity chromatography resin, wherein said affinity ligand is a 13 kD yeast derived Fab antibody fragment directed to the Factor VIII, wherein the affinity chromatography comprises the following steps:
binding of a starting solution comprising the Factor VIII with a ratio of FVIII:C/FVIII:Ag in the range of about 0.6 to about 0.7 to the affinity chromatography resin occurs under low salt conditions equivalent to a concentration of 0.1-0.5 mol/kg sodium chloride,
washing the affinity chromatography resin under increased salt concentration equivalent to in the range of 0.3-4 mol/kg sodium chloride for removal of the light chain, and
eluting and collecting Factor VIII in a separate fraction by employing a salt concentration equivalent to in the range of 0.5-4 mol/kg sodium chloride or $MgCL_2$ in combination with 40-60% of an alcohol, and wherein the load of the affinity chromatography resin with biologically active Factor VIII is at least 10,000 IU/ml resin;
wherein the Factor VIII product has a Factor VIII monomer content of ≥98% and no aggregated Factor VIII.

2. The process according to claim 1 further comprising at least one chromatographic step employing a size exclusion chromatography.

3. The process of claim 1 wherein the Factor VIII is a complex of a light chain and a heavy chain and the ratio of FVIII:C/FVIII:Ag of at least 0.7 in the Factor VIII product results from depletion of the Factor VIII light chain, the Factor VIII heavy chain and/or dissociated Factor VIII light chain/Factor VIII heavy chain from the complex.

4. The process according to claim 3 wherein the affinity chromatography resin is based on a cross linked agarose matrix with an average particle size of 74 μm and the 13 kD yeast derived Fab antibody fragment affinity ligand is bound to the matrix through a hydrophilic spacer arm to make the ligand more available for binding to the Factor VIII and the affinity ligand binds to the Factor VIII light chain of the biologically active Factor VIII.

5. The process according to claim 1, wherein the chromatographic step employing an affinity chromatography resin comprises at least two of the following conditions;
buffer conditions during Factor VIII binding: 0.1-0.5 mol/kg NaCl, 0.01-0.05 mol/kg $CaCl_2$, 0.01-0.05 mol/kg L-histidine, 0.005-0.05% (w/w) Polysorbate 80, 0.5-2% Triton X-100, 0.1-1% TNBP at pH 6.2-6.8;
buffer conditions during wash: 0.5-4 mol/kg NaCl, 0.01-0.05 mol/kg $CaCl_2$, 0.01-0.05 mol/kg L-histidine, 0.005-0.05% (w/w) Polysorbate 80 at pH 6.2-6.8; and
buffer conditions during Factor VIII elution: 0.5-4 mol/kg NaCl, 40-60% ethylene glycol, 0.01-0.05 mol/kg $CaCl_2$), 0.01-0.05 mol/kg L-histidine, 0.005-0.05% (w/w) Polysorbate 80 at pH 6.2-6.8.

6. The process according to claim 1 wherein the affinity chromatography resin is a cross-linked agarose base matrix.

7. The process according to claim 1, wherein Factor VIII comprises a light chain part and a heavy chain part and the affinity ligand binds to said light chain part of Factor VIII and removes it specifically.

8. The process of claim 1 further comprising at least one chromatographic step employing an anion exchange chromatography, wherein the anion exchange chromatography is performed under conditions that Factor VIII binds to the anion exchange chromatography resin and that biologically inactive forms are removed from the anion exchange chromatography resin either before or after elution of biologically active Factor VIII, wherein
loading Factor VIII is performed under low salt conditions equivalent to a concentration of 0.01-0.15 mol/kg sodium chloride for binding of Factor VIII and removal of inactive forms of Factor VIII,
washing the anion exchange chromatography resin is performed under medium salt conditions equivalent to a concentration of 0.15-0.3 mol/kg sodium chloride for removal of inactive forms of Factor VIII, and eluting and collecting intact monomeric Factor VIII from the anion exchange chromatography resin in a separate fraction is performed by employing high salt conditions equivalent to a concentration of 0.3-1 mol/kg sodium chloride.

9. The process of claim 8 wherein the anion exchange chromatography step comprises at least two of the following chromatographic conditions:

a resin load of biologically active Factor VIII of at least 10,000 IU/ml resin, buffer conditions during Factor VIII loading: 0.05-0.15 mol/kg NaCl, 0.01-0.05 mol/kg $CaCl_2$, 0.01-0.05 mol/kg L-histidine, 0.005-0.05% (w/w) Polysorbate 80 at pH 6.0-7.5;

buffer conditions during wash: 0.15-0.3 mol/kg NaCl, 0.01-0.05 mol/kg $CaCl_2$, 0.01-0.05 mol/kg L-histidine, 0.005-0.05% (w/w) Polysorbate 80 at pH 6.0-7.5;

buffer conditions during Factor VIII elution: 0.3-0.5 mol/kg NaCl, 0.01-0.05 mol/kg $CaCl_2$, 0.01-0.05 mol/kg L-histidine, 0.005-0.05% (w/w) Polysorbate 80 at pH 6.0-7.5.

10. The process of claim 8 wherein the anion exchange chromatography resin is a strong anion exchanger with a quaternary amine ion as ligand coupled to a cross linked 6% agarose matrix with a spherical diameter of 45-165 μm, with a total ion binding capacity of 0.18-0.25 mmol/ml.

11. The process of claim 2 wherein the size exclusion chromatography step comprises at least two of the following chromatographic conditions:

a sample load of 4-8% of a column volume;
a column height of 60-90 cm;
a biologically active Factor VIII concentration in the sample load of at least 10,000 IU/ml;

a column equilibration buffer for optimal aggregation of inactive forms of Factor VIII: 0.2-0.7 mol/kg NaCl, 0.01-0.05 mol/kg $CaCl_2$), 0.01-0.05 mol/kg sodium citrate, 0.5-2% (w/w) sucrose, 0.5-2% (w/w) L-arginine, 0.1-1% (w/w) Poloxamer 188 at pH 6.0-7.5, wherein the biologically active Factor VIII is collected in the monomeric form, whereas inactive Factor VIII is found either in the aggregated peak and/or in the fragmented peak fraction of the size exclusion chromatography step; and Factor VIII monomer collection starts when 30-40 mAU absorbance peak is recorded after the column and stops when absorbance peak is reverting back to 1-40 mAU, relating to 2-3 times the amount of sample application.

12. The process according to claim 2 wherein the size exclusion chromatography resin is a spherical crosslinked Agarose/Dextran media with a mean diameter of 34 μm and an optimal separation range between 10,000-600,000 Dalton.

13. The process of claim 1, wherein the alcohol is selected from ethylene glycol, propylene glycol and mixtures thereof.

14. The process of claim 1, wherein the alcohol ethylene glycol.

15. The process of claim 1, wherein the increased salt concentration equivalent to in the range of 0.3-4 mol/kg sodium chloride is increased salt concentration in the range of 0.3-4 mol/kg sodium chloride, and the salt concentration equivalent to in the range of 0.5-4 mol/kg sodium chloride or $MgCL_2$ is a salt concentration in the range of 0.5-4 mol/kg sodium chloride.

* * * * *